(12) United States Patent
Masia et al.

(10) Patent No.: US 10,786,415 B2
(45) Date of Patent: Sep. 29, 2020

(54) SYSTEMS AND METHODS FOR ASSESSING AND TRAINING WRIST JOINT PROPRIOCEPTIVE FUNCTION

(71) Applicants: Regents of the University of Minnesota, Minneapolis, MN (US); Nanyang Technological University, Singapore (SG); Italian Institute of Technology, Genoa (IT); University of Genoa, Genoa (IT)

(72) Inventors: Lorenzo Masia, Singapore (SG); Juergen Konczak, Minneapolis, MN (US); Giulio Sandini, Genoa (IT); Leonardo Cappello, Arezzo (IT)

(73) Assignees: Regents of the University of Minnesota, Minneapolis, MN (US); Nanyang Technological University, Singapore (SG); Italian Institute of Technology (IT); University of Genoa (IT)

( * ) Notice: Subject to any disclaimer, the term of this patent is extended or adjusted under 35 U.S.C. 154(b) by 1120 days.

(21) Appl. No.: 15/073,262

(22) Filed: Mar. 17, 2016

(65) Prior Publication Data
US 2016/0270999 A1    Sep. 22, 2016

Related U.S. Application Data

(60) Provisional application No. 62/136,065, filed on Mar. 20, 2015.

(51) Int. Cl.
*A61H 1/02* (2006.01)
*G06F 19/00* (2018.01)

(52) U.S. Cl.
CPC ....... *A61H 1/0285* (2013.01); *G06F 19/3481* (2013.01); *A61H 2201/1635* (2013.01);
(Continued)

(58) Field of Classification Search
CPC .......... A61H 1/00; A61H 1/02; A61H 1/0274; A61H 1/0285; A61H 2201/1635;
(Continued)

(56) References Cited

U.S. PATENT DOCUMENTS 4,885,687 A * 12/1989 Carey .................. A61B 5/225
434/261
5,466,213 A    11/1995 Hogan et al.
(Continued)

FOREIGN PATENT DOCUMENTS

WO      2006066401      6/2006
WO      2010040416      4/2010
WO      WO-2016117998 A1 *  7/2016  ........... A61H 1/0274

OTHER PUBLICATIONS

Squeri V, Masia L, Casadio M, Morasso P, Vergaro E (2010) Force-Field Compensation in a Manual Tracking Task. PLoS One 5(6):e11189. https://doi.org/10.1371/journal.pone.0011189 (Year: 2010).*

(Continued)

*Primary Examiner* — Justine R Yu
*Assistant Examiner* — Matthew R Moon
(74) *Attorney, Agent, or Firm* — Dicke, Billig & Czaja, PLLC

(57) ABSTRACT

A comprehensive system for treatment of wrist joint proprioception. The system includes a manipulandum unit and a controller. The unit includes a base, a handle, a linkage assembly, and motors. The base supports a subject's forearm, and the handle is gripped by the palm. The linkage assembly connects the handle to the base, and establishes three DOFs. The motors are operatively connected to the linkage assembly. The controller is programmed to actuate, and receive feedback information from, each of the plurality of motors. Further, the controller is programmed to perform wrist proprioception assessment operations by actuating the
(Continued)

plurality of motors to effectuate movement of the handle relative to the base in a prescribed manner indicative of position motion sense acuity as an objective measure of wrist proprioception functioning. The controller is optionally further programmed to perform rehabilitation training via controlled operation of the unit and a virtually reality environment.

16 Claims, 18 Drawing Sheets

(52) U.S. Cl.
CPC ............... *A61H 2201/5038* (2013.01); *A61H 2201/5069* (2013.01); *A61H 2201/5079* (2013.01)

(58) Field of Classification Search
CPC ...... A61H 1/50; A61H 1/5038; A61H 1/5069; A61H 1/5079; A61H 2205/06; A61H 2205/065; A61H 2201/0107; A61H 2201/0157; A61H 2201/1207; A61H 2201/1671; A61H 2201/1673; A61H 2201/5064; A63B 26/003; G09B 19/003; A61B 5/11; A61B 5/1101
USPC ........................ 434/258; 600/587, 595; 345/6
See application file for complete search history.

(56) References Cited

U.S. PATENT DOCUMENTS

| | | | | |
|---|---|---|---|---|
| 5,695,431 | A * | 12/1997 | Bond | A63B 21/00178 482/1 |
| 5,713,370 | A * | 2/1998 | Cook | A61B 5/0488 482/114 |
| 6,599,255 | B2 * | 7/2003 | Zhang | A61H 1/02 600/587 |
| 6,613,000 | B1 | 9/2003 | Reinkensmeyer et al. | |
| 7,566,311 | B2 | 7/2009 | Cordo | |
| 7,618,381 | B2 | 11/2009 | Krebs et al. | |
| 7,725,175 | B2 | 5/2010 | Koeneman et al. | |
| 7,951,096 | B2 * | 5/2011 | Ju | A61H 1/0274 601/33 |
| 8,083,694 | B2 | 12/2011 | Peles | |
| 8,214,029 | B2 | 7/2012 | Koeneman et al. | |
| 8,277,396 | B2 * | 10/2012 | Scott | A61B 5/1121 600/595 |
| 8,597,212 | B2 * | 12/2013 | Kawakami | A61F 5/013 601/23 |
| 2006/0106326 | A1 | 5/2006 | Krebs et al. | |
| 2007/0066918 | A1 * | 3/2007 | Dewald | A61H 1/02 601/5 |
| 2009/0306548 | A1 * | 12/2009 | Bhugra | A61H 1/024 600/587 |
| 2011/0112441 | A1 * | 5/2011 | Burdea | A63B 21/06 600/595 |
| 2011/0137196 | A1 | 6/2011 | Kakei et al. | |
| 2011/0264018 | A1 * | 10/2011 | Matjacic | A61H 1/0274 601/40 |
| 2013/0012362 | A1 * | 1/2013 | Ju | A61H 1/0285 482/49 |
| 2014/0240109 | A1 | 8/2014 | Aviles et al. | |
| 2014/0296750 | A1 | 10/2014 | Einav et al. | |
| 2015/0133828 | A1 * | 5/2015 | Hachisuka | A61H 1/0285 601/5 |
| 2015/0359697 | A1 * | 12/2015 | Celik | A61H 1/0285 601/33 |
| 2017/0132947 | A1 * | 5/2017 | Maeda | A61H 1/02 |
| 2017/0209327 | A1 * | 7/2017 | Hou | A61H 1/00 |

OTHER PUBLICATIONS

The International Search Report and Written Opinion for related Application No. PCT/US2016/022924 dated Jun. 14, 2016 (12 pgs).
E Hagert, "Proprioception of the Wrist Joint: A Review of Current Concepts and Possible Implications on the Rehabilitation of the Wrist", Journal of Hand Therapy, Jan.-Mar. 2010, 16 pgs.
E Hagert, "Proprioception of the Wrist Joint: A Review of Possible Implications on the Rehabilitation of the Wrist and Hand", International Academy of Orthopedic Medicine (IAOM), May 9, 2014, 7 pgs.
V Squeri et al., "Wrist Rehabilitation in Chronic Stroke Patients by Means of Adaptive, Progressive Robot-Aided Therapy", IEEE Transactions on Neural Systems and Rehabilitation Engineering, vol. 22, No. 2, Mar. 2014, pp. 312-325.
DJ Reinkensmeyer et al., "Robotics, Motor Learning, and Neurologic Recovery", Annual Review of Biomedical Engineering, 2004, 6:497-525.
L Cappello, "Robot-Aided Assessment of Wrist Proprioception", Frontiers in Human Neuroscience, ISSN: 1662-5161, Sep. 4, 2014, 22 pgs.
Krebs et al., "Robot-Aided Neurorehabilitation: a Robot for Wrist Rehabilitation," IEEE Transactions on Neural Systems and Rehabilitation Engineering, vol. 15, No. 3, pp. 327-335 (Sep. 2007).
Brewer et al., "Poststroke Upper Extremity Rehabilitation: A Review of Robotic Systems and Clinical Results," Topics in Stroke Rehabilitation, pp. 22-44 (Nov.-Dec. 2007).
Squeri et al., "Integrating Proprioceptive Assessment with Proprioceptive Training of Stroke Patients," IEEE International Conference on Rehabilitation Robotics, pp. 6 (Jun. 29-Jul. 1, 2011).
Masia et al., "Eye-Hand Coordination During Dynamic Visuomotor Rotations," PLoS One, vol. 4, Issue 9, pp. 1-11 (Sep. 2009). <www.plosone.org>.
Masia et al., "Performance Adaptive Training Control Strategy for Recovering Wrist Movements in Stroke Patients: A Preliminary, Feasibility Study," Journal of NeuroEngineering and Rehabilitation, 6:44, pp. 11 (Dec. 7, 2009). (http://www.jneuroengrehab.com/content/6/1/44>.
Masia et al., "Wrist Coordination in a Kinematically Redundant Stabilization Task," IEEE Transactions on Haptics, vol. 5, No. 3, pp. 231-239 (Jul.-Sep. 2012).
Cappello et al., "Robot-Aided Assessment of Wrist Proprioception," Frontiers in Human Neuroscience, vol. 9, Article 198, pp. 8 (Apr. 2015). <www.frontiersin.org>.

* cited by examiner

SYSTEMS AND METHODS FOR ASSESSING AND TRAINING WRIST JOINT PROPRIOCEPTIVE FUNCTION

CROSS-REFERENCE TO RELATED APPLICATIONS

This Non-Provisional patent application claims the benefit of the filing date of U.S. Provisional Patent Application Ser. No. 62/136,065, filed Mar. 20, 2015, entitled "Systems and Methods for Assessing and Training Wrist Joint Proprioceptive Function," which is herein incorporated by reference.

BACKGROUND

The present disclosure relates to automated manipulation of a human subject's wrist joint. More particularly, it relates to automated systems and methods for assessing the proprioceptive status or function at the wrist joint, and optionally for improving proprioceptive function through proprioceptive sensory training.

Broadly defined, proprioception refers to the sense of body awareness. This awareness is based on signals from the receptors embedded in joints, muscles, tendons and skin. Classically, four properties of proprioceptive function are distinguished: passive motion sense, active motion sense, limb position sense, and the sense of heaviness. Joint proprioceptive signals are essential for intact monosynaptic muscle stretch reflexes and polysynaptic postural reflexes that are involved in balance control during standing and locomotion. They are also vital for controlling fine-motor voluntary movements such as grasping, reaching or writing with the hand.

It is well established that the processing of proprioceptive information is important for the neural control of movement. Conversely, the loss of proprioception negatively impacts the reflexive control of balance, and severely impairs spatial as well as temporal aspects of voluntary movements. Clinical studies have documented that proprioceptive loss debilitates even seemingly simple actions like cutting, and that such impairments are not restored by using vision as a sensory substitute. Numerous neurological and orthopedic conditions are associated with proprioceptive and kinaesthetic impairment such as stroke, Parkinson's disease, focal dystonia, peripheral sensory neuropathies, or orthopedic injuries to ligaments, joint capsules and muscles.

Despite the recognition that proprioceptive deficits are the most frequent long-term side effect after brain damage, there is no established, precise method available in clinical settings to assess proprioceptive function. Recognized clinical tests to assess proprioceptive acuity are coarse. For example, the Nottingham Sensory Assessment (NSA) test and the Rivermead Assessment of Somatosensory Performance (RASP) test are based on detecting a subject's capability to discriminate the upwards and downwards position of a single limb segment (i.e., finger or toe). Although the loss of limb proprioception may severely impact the effectiveness of available rehabilitation protocols aiming to restore motor function, the presence of an objective, accurate and reliable method to assess proprioceptive function is still missing in rehabilitation practice.

An alternative approach to assess proprioceptive function is to obtain psychophysical thresholds for joint position sense (JPS), motion sense (kinesthesia), and sense of tension or force. These threshold hunting methods yield two types of thresholds: a detection threshold, which is the smallest perceivable stimulus change (e.g., a position, motion or force), and a discrimination threshold, which is the just noticeable difference (JND) between two perceived stimuli. The detection threshold is considered a measure of the sensitivity, while the discrimination threshold represents a measure of acuity. In contrast to joint matching methods that rely on active motion of the test person, threshold hunting paradigms often use specialized equipment that passively moves a person's limb in a highly controlled manner. Objective measurements of JPS have been obtained through the use of various instruments such as goniometers or inclinometers. Joint matching paradigms that mimic clinical testing have been most common to determine a JND threshold for JPS, but not for joint motion sense.

However, recent research indicated that psychophysical threshold methods yield a more precise estimate of a limb position discrimination threshold than joint position matching methods, and passive motion testing results in lower thresholds than tests involving active motion.

More recently, it has been suggested that haptic technology or robotic devices may be useful for obtaining sense thresholds of the hand or fingers. However, most robotic devices have focused on testing single Degree of Freedom (DOF) joints such as the elbow or were only capable of displacing or moving a joint in a single plane (e.g., dorsiflexion/plantarflexion of the ankle). This approach overtly restricts the types of joints that can be investigated, or it provides only partial information on the proprioceptive status of a joint. Moreover, while robotic-based rehabilitation systems have been suggested that may entail active limb movement with more than a single DOF, such systems do not consider, let alone address, the possibility of automated assessment of proprioceptive function of a multi-plane of movement joint, such as the wrist joint.

In light of the above, a need exists for proprioceptive function assessment systems for joints having more than one plane of movement, as well as for systems having an integrated capability of assessment of proprioceptive function and proprioceptive training.

SUMMARY

Some aspects of the present disclosure are directed toward a wrist joint proprioception system. The system includes a manipulandum unit and a controller. The manipulandum unit includes a base, a handle, a linkage assembly, and a plurality of motors. The base is configured to support a subject's forearm. The handle is configured to be gripped by a subject's hand. The linkage assembly connects the handle to the base, and establishes three degrees of freedom of movement of the handle relative to the base. Each of the plurality of motors is operatively connected to the linkage assembly. The controller is electronically connected to the manipulandum unit and is programmed to actuate, and receive feedback information from, each of the plurality of motors. Further, the controller is programmed to perform a proprioception assessment operation for objectively measuring proprioceptive function of a subject's wrist joint by actuating at least one of the plurality of motors to effectuate movement of the handle relative to the base in a predetermined manner. The assessment operation includes a position sense routine in which the plurality of motors is actuated by the controller to establish a reference position of the handle relative to the base. The position sense routine further includes one or more of the motors moving the handle about a first axis from the reference position to a standard position, and from the standard position back to the reference position. The position sense routine further includes one or more of the motors moving the handle about the first axis from the reference position to a first comparison position, and from the first comparison position to the reference position. In this regard, the controller is programmed to establish a pre-determined difference between the standard position and the first comparison position. A subject's ability to perceive the difference is indicative of a subject's proprioceptive wrist position sense acuity as an objective measure of a subject's wrist joint proprioceptive function.

In some embodiments, the proprioceptive function implicated by the position sense routine relates to the subject's perception of an absolute change in an articulated position of the wrist joint, and in other embodiments relates to discrimination between different articulated positions of the wrist joint. In yet other embodiments, the controller is programmed to perform one or more motion sense routines that implicate a subject's ability to perceive motion of the wrist joint and/or discrimination between different velocities of movement. In yet other embodiments, the controller is programmed to perform a rehabilitation training operation via controlled operation of the manipulandum unit and a virtually reality environment. In yet other embodiments, the manipulandum unit includes a first motor connected to the linkage assembly so as to control articulation of the handle about an FE axis of the unit (inducing flexion-extension of the subject's wrist joint), second and third motors connected to the linkage assembly so as to control articulation of the handle about an AA axis of the unit (inducing abduction-adduction of the subject's wrist joint), and a fourth motor connected to the linkage assembly so as to control articulation of the handle about a PS axis of the unit (inducing pronation-supination of the subject's hand).

DETAILED DESCRIPTION

Figure 1:
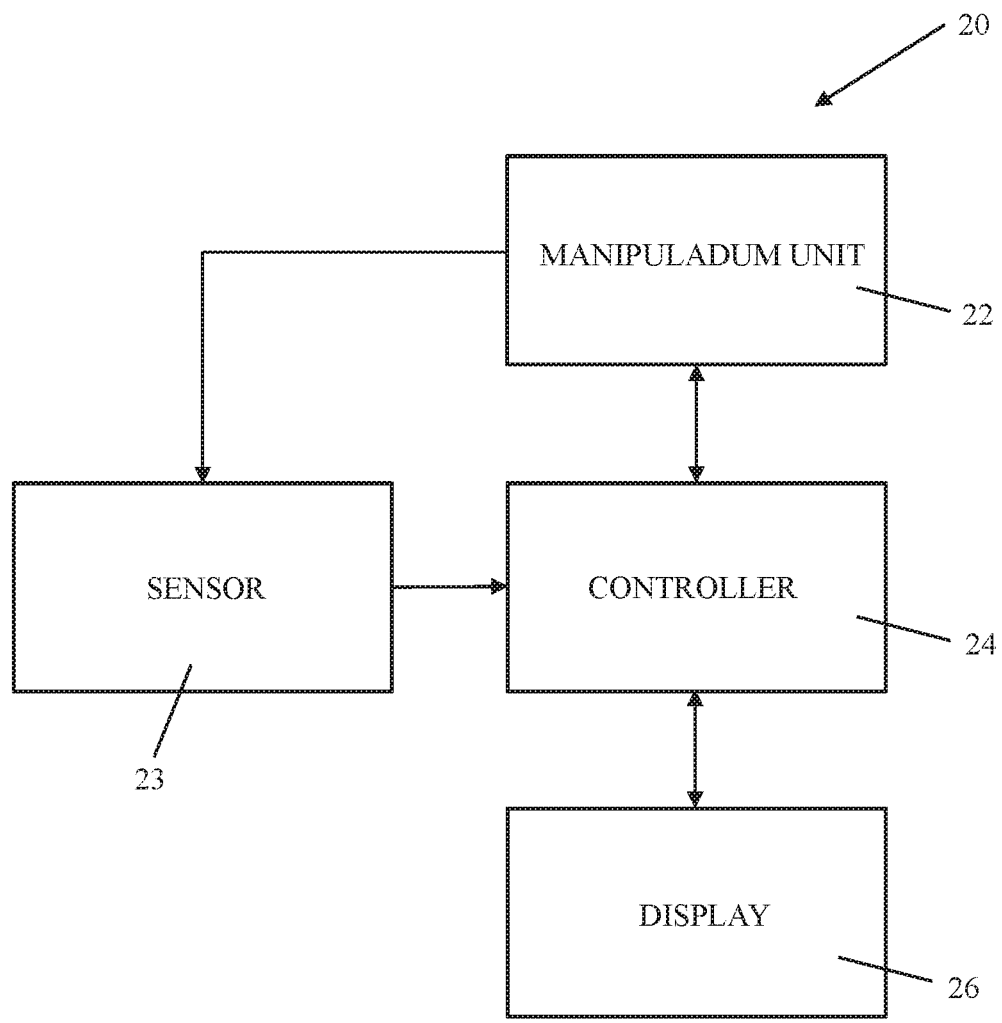
FIG. 1 is a block diagram of a wrist joint proprioception system in accordance with principles of the present disclosure.

One embodiment of a wrist joint proprioception system 20 function in accordance with principles of the present disclosure is shown in block form in FIG. 1. The systems 20 of the present disclosure include a manipulandum unit 22 and a controller 24. Details on the various components are provided below. In general terms, however, the manipulandum unit 22 is a robotic-type device, generally configured to receive a subject's forearm and hand, and to establish a three degrees-of-freedom (DOF) environment in which the subject's wrist can be controllably and independently manipulated about three axes of rotation (in accord to and within the anatomical range of motion of natural planes of wrist movements). The controller 24 is programmed to control operation of the manipulandum unit 22 in a pre-determined fashion. In this regard, the controller 24 can be programmed to effectuate performance of one or more proprioceptive assessment routines at the manipulandum unit 22 and from which proprioceptive function of the subject's wrist is objectively assessed in a standardized manner. In some embodiments, the controller 24 is further programmed effectuate performance of one or more proprioceptive rehabilitation training routines at the manipulandum unit 22 and selected to improve motor function of the subject's wrist. In related embodiments, the system 20 can include one or more displays 26 that are operated by the controller to create a virtual reality environment as part of the rehabilitation training.

Figure 2A:
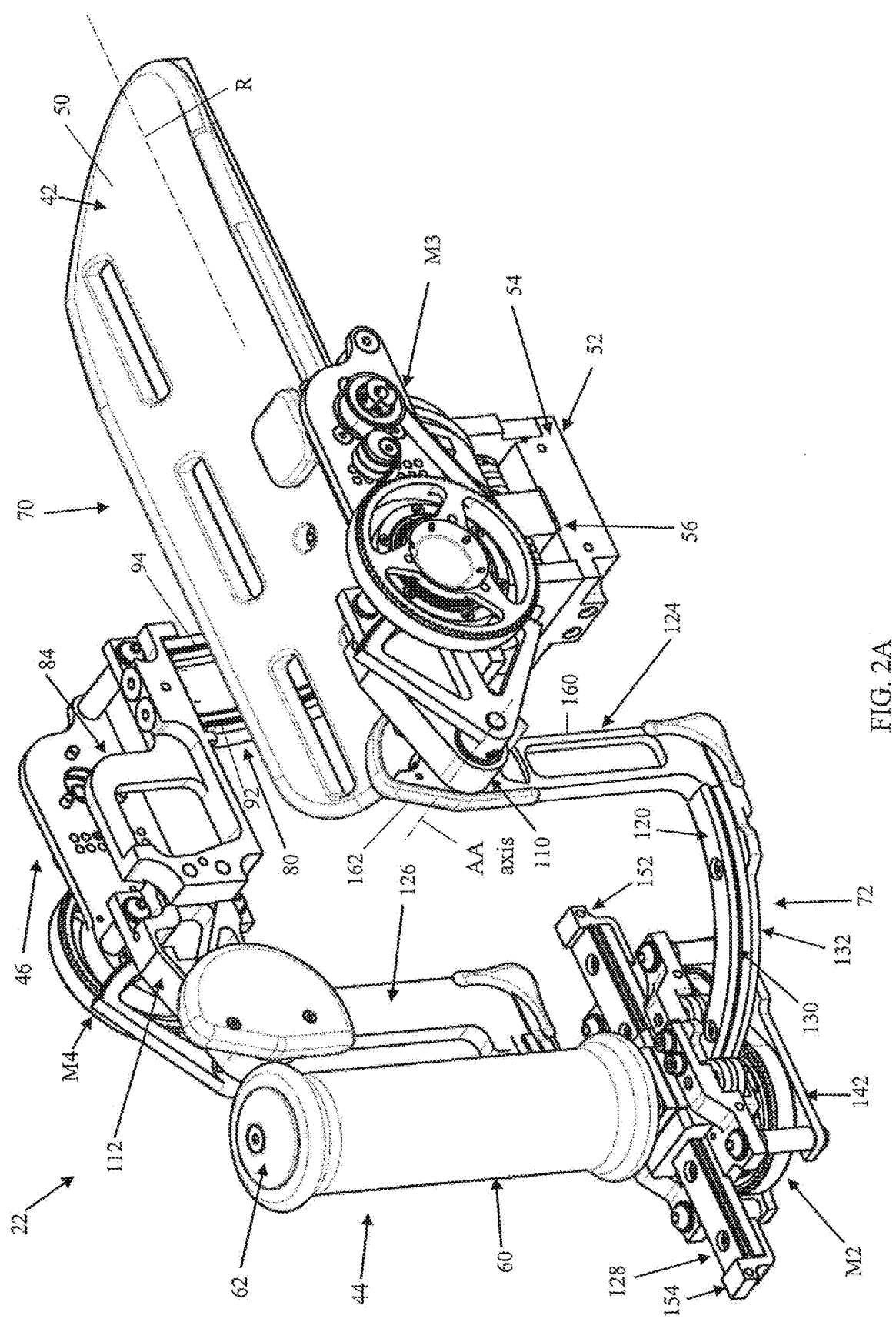
FIGS. 2A and 2B are perspective views of a manipulandum unit useful with the system of FIG. 1.
Figure 2B:
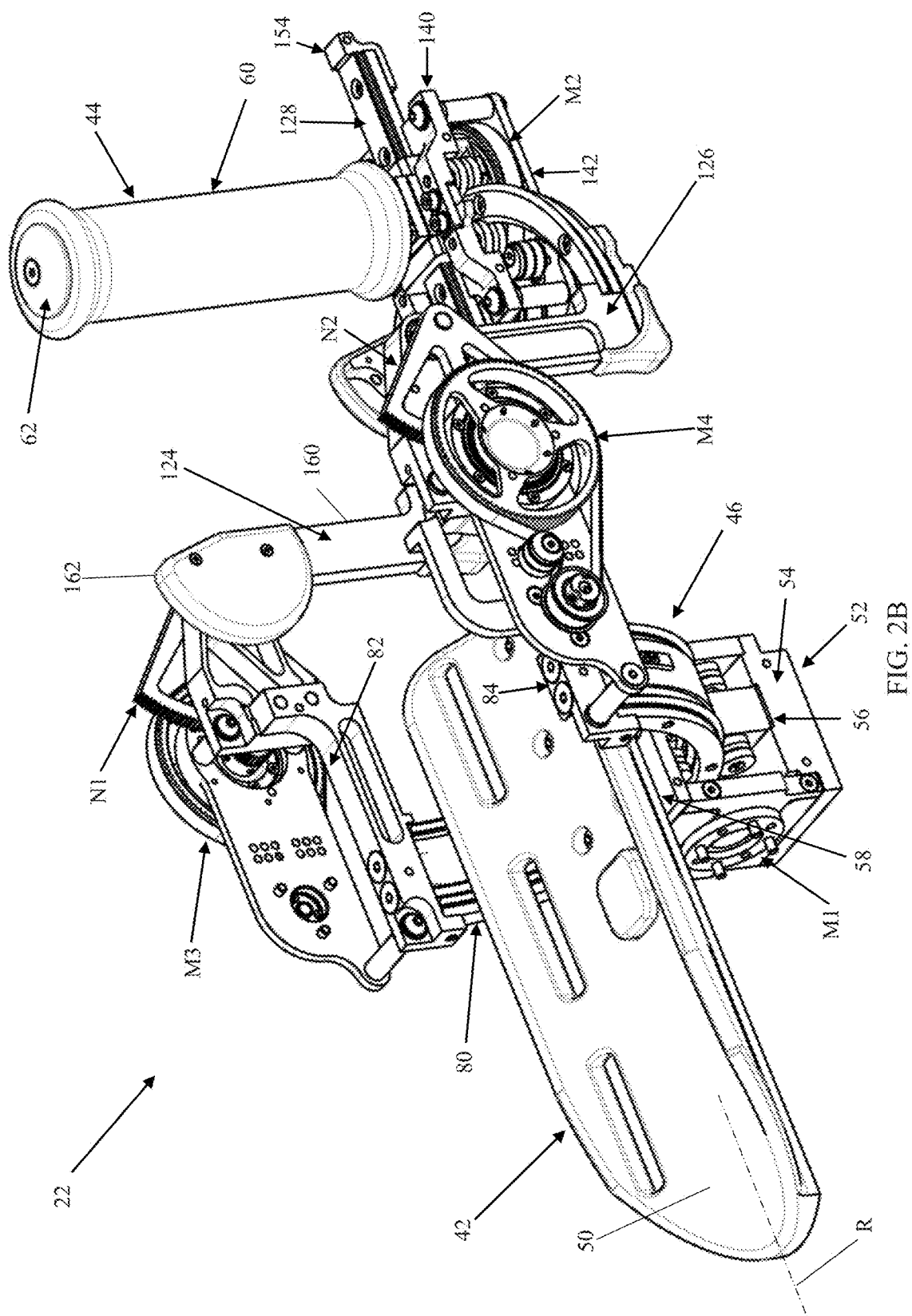

One embodiment of the manipulandum unit 22 useful with the systems of the present disclosure is shown in FIGS. 2A and 2B. The unit 22 generally includes a base or splint 42, a handle 44, a linkage assembly 46 (referenced generally), and a plurality of motors (not shown). The linkage assembly 46 connects the handle 44 with the base 42, and establishes three DOF of movement the handle 44 relative to the base 42. As made clear below, the three axes about which the three DOFs are established at the manipulandum unit 22 can be designated in accordance with three axes of wrist joint rotation when manipulated by the unit 22; namely, pronation/supination (PS), flexion/extension (FE), and abduction/adduction (AA). The motors are connected to the linkage assembly 46 and dictate or actuate movement of the handle 44 via the linkage assembly 46.

The base 42 is generally sized and shaped to ergonomically receive a human forearm, and optionally presents or provides a support surface 50 against which a subject's forearm will comfortably rest while the subject's hand or palm is grasping the handle 44. The support surface 50 can have the curved shape as shown. For reasons made clear below, the base 42 can be viewed as establishing a reference axis R relative to which movement axes of the linkage assembly 46 can be defined. The reference axis R represents an approximate longitudinal centerline of the support surface 50; a centerline of a subject's forearm will be substantially parallel with the reference axis R when resting on the support surface 50 (it being understood that the forearm centerline will necessarily be above (relative to the orientation of the views) the reference axis R when the forearm lies on the support surface 50).

In some embodiments, the base 42 can be attached to an optional carrier 52. The carrier 52 includes a floor 54, a bracket 56 and a platform 58. The floor 54 is configured to promote rigid attachment of the carrier 52 (and thus the base 42) to a stationary surface such as a tabletop, whereas the platform 58 robustly supports the base 42. The bracket 56 supports the platform 58 relative to the floor 54, and is adapted to receive and support portions of the linkage assembly 46 and a corresponding one of the motors as described below. The carrier 52 can assume a wide variety of other forms commensurate with a construction of the base 42 and/or the linkage assembly 46. In other embodiments, the carrier 52 can be omitted.

The handle 44 can assume various forms and is generally configured to promote ergonomic gripping thereof by a subject's hand or palm. In some embodiments, the handle 44 can include a grip member 60 and a post 62. The grip member 60 can be formed of a compliant material (e.g., foam, rubber, etc.), and can be contoured for comfortable gripping by a subject's hand. The grip member 60 is disposed over the post 62 that in turn is adapted for attachment to the linkage assembly 46 as described below.

Figure 3:
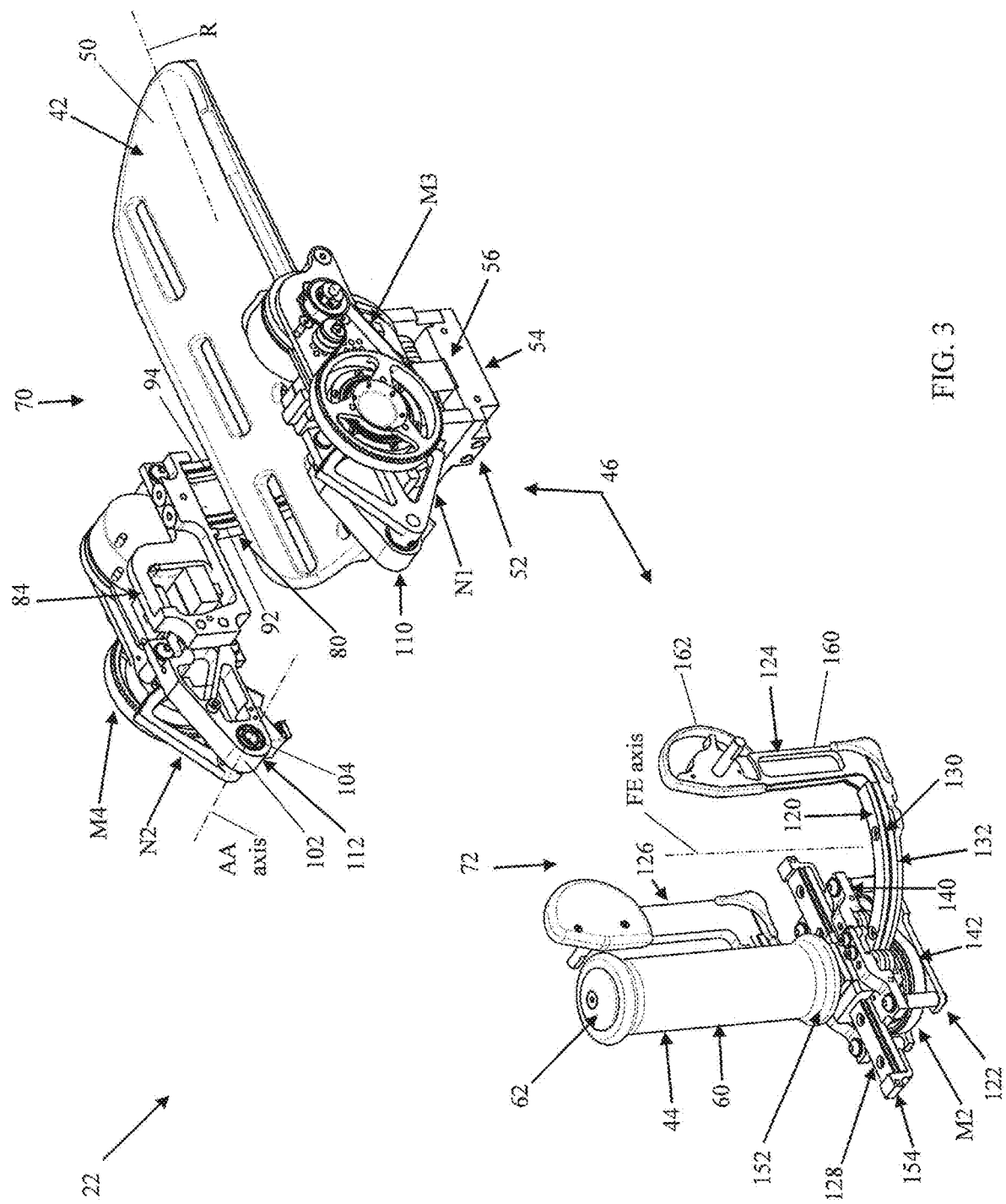
FIG. 3 is a partially exploded view of the manipulandum unit of FIG. 2A.

The linkage assembly 46 interconnects the base 42 and the handle 44, and generally includes or provides a PS transmission sub-assembly 70 and a FE transmission sub-assembly 72 as best reflected in FIG. 3. As described below, connection between the PS transmission sub-assembly 70 and the FE transmission sub-assembly 72 establishes an AA transmission arrangement.

Figure 4:
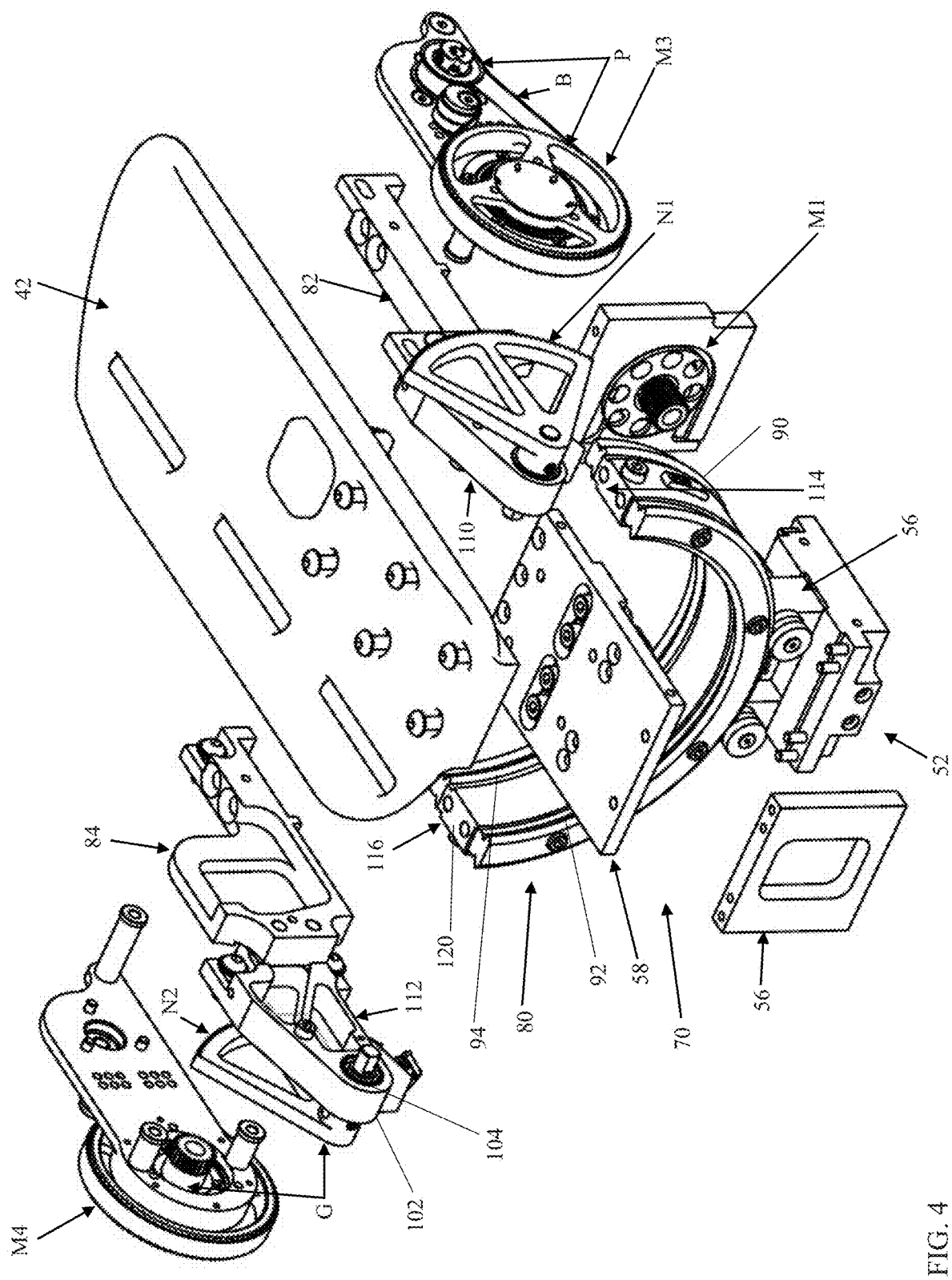
FIG. 4 is an exploded view of a PS transmission sub-assembly of the manipulandum unit of FIG. 2A.

With additional reference to the exploded view of FIG. 4, the PS transmission sub-assembly 70 includes a track 80 and opposing, first and second arms 82, 84. The track 80 can assume various forms configured for translatable coupling with the output shaft of a motor (not shown). The track 80 can have the semi-circular or U-shape shown, and in some embodiments includes first and second track members 90, 92. The track members 90, 92 can have an identical size and shape (e.g., the semi-circular or U-shape reflected in the views). With optional embodiments of the manipulandum unit 40 that otherwise include the carrier 52, the track members 90, 92 are configured to be slidably mounted relative to the carrier 52, for example with the first track member 90 being disposed within the bracket 56 and the second track member 92 located outside of the bracket 56. Regardless, assembly of the track 80 relative to the carrier 52 is such that the track 80 can rotate relative to the carrier 52 as described below, for example by pivoting or rotating about a centerline of the semi-circle or U shape generated by the track 80. In this regard, the track 80 is configured in tandem with the mounting arrangement relative to the carrier 52 such that the centerline of the shape of the track 80 (and about which the track 80 is articulated) is substantially parallel with but above (relative to the orientation of the views) the reference axis R of the base 42. For example, the centerline of the track 80 shape is generally located to be in-line with an expected centerline of a subject's forearm when resting on the support surface 52 (it being understood that different subjects will have differently-sized forearms such that the centerline of the track 80 will invariably be slightly offset with the subject's forearm centerline). Finally, at least the first track member 90 incorporates mounting features appropriate for connection with the motor (not shown) output shaft, such as a slot 94.

The arms 82, 84 can be substantially identical (e.g., mirror images), generally configured for connection to opposite ends, respectively, of the track 80. As identified for the second arm 84, each of the arms 82, 84 are connected to the respective mounting rings 110, 112 that each terminate at or form a leading end 102. The leading end 102 is configured to facilitate a pivotable or hinged connection with a corresponding component of the FE transmission sub-assembly 72. For example, the leading end 102 can include or form a bore 104 sized and shaped to rotatably receive a pin, shaft or other mounting body (not shown). Other mounting techniques are also acceptable. Regardless, a common AA axis (shown in FIG. 3) of the manipulandum unit 22 is established at the leading end 102 of the arms 82, 84 and about which the FE transmission sub-assembly 72 can pivot relative to the arms 82, 84 (and thus relative to the PS transmission sub-assembly 70).

Each of the arms 82, 84 is optionally configured to be rigidly connected to or carry a motor M3, M4, locating an output shaft of the motor M3, M4 to interface with a corresponding component carried by, or connected to, the FE transmission sub-assembly 72. Each motor M3, M4 can be mounted to the corresponding arm 82, 84 in various fashions. In some embodiments, for example, the mounting ring 110 is attached to and extends from the first arm 82, and the identical mounting ring 112 is attached to and extends from the second arm 84. The mounting rings 110, 112 can assume any format appropriate for rigidly supporting the corresponding motor, and can be located at any location along a length of the corresponding arm body 102 appropriate for spatially locating the motor's output shaft at a desired position relative to the leading end 102 for interfacing with the FE transmission sub-assembly 72 as described below.

The arms 82, 84 can be connected to the track 80 in various manners. In some embodiments, a fixed-type connection is provided, for example by a connector body 114 coupling the first arm 82 to a first end of the track 80, and a connector body 116 coupling the second arm 84 to an opposite, second end of the track 80. The connector bodies 114, 116 can be identical. As identified for the second connector body 116 in FIG. 4, each of the connector bodies 114, 116 includes a platform 120. The platform 120 provides a flat surface for rigidly receiving and maintaining the arm 82 and 84. Other mounting constructions are equally acceptable, and in other embodiments the arms 82, 84 can be rigidly fixed to the track 80.

Figure 5:
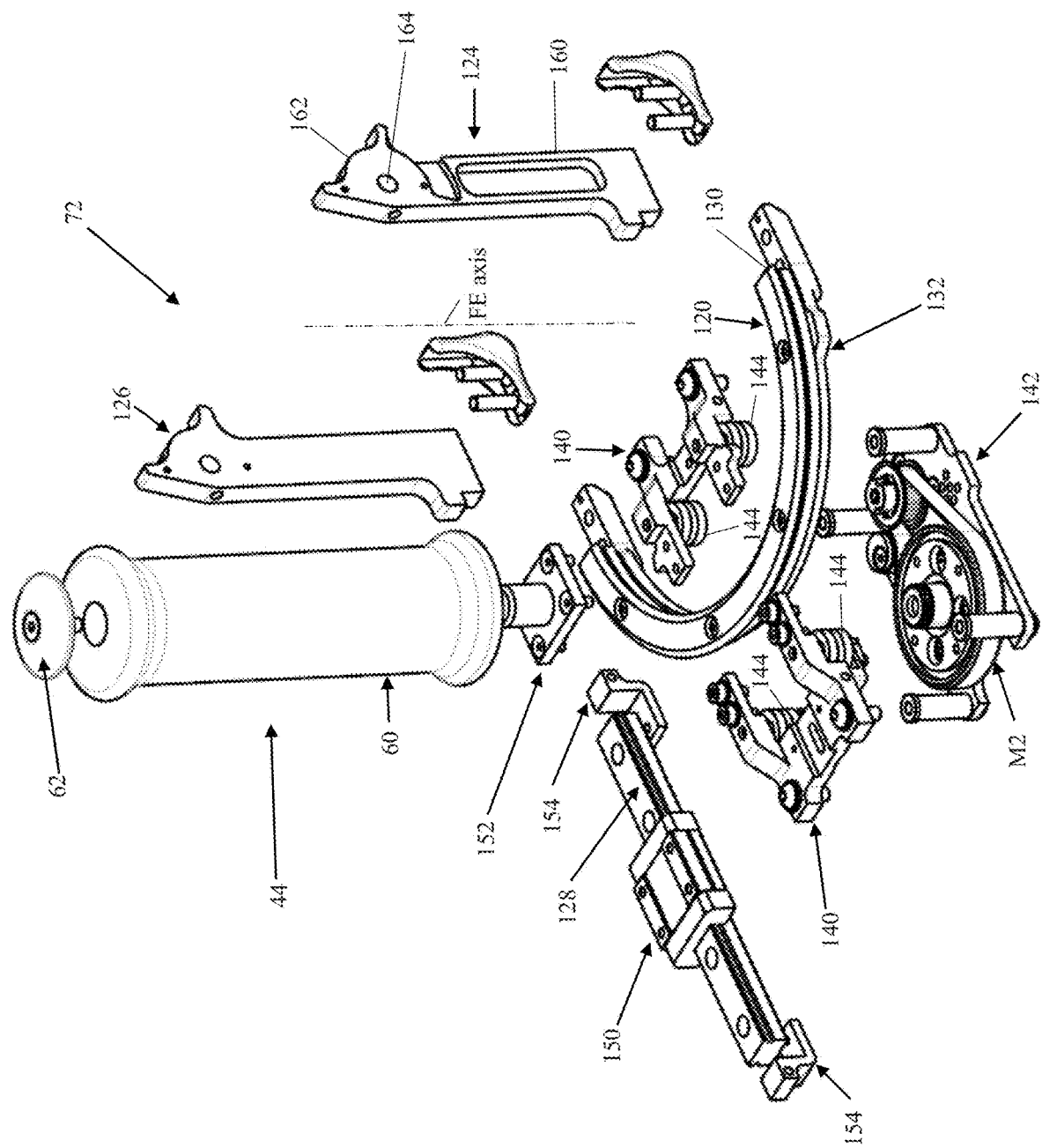
FIG. 5 is an exploded view of an FE transmission sub-assembly of the manipulandum unit of FIG. 2A.

One embodiment of the FE transmission sub-assembly 72 is shown in greater detail in FIG. 5 (along with the handle 44). With cross-reference between FIGS. 3 and 5, the FE transmission sub-assembly 72 includes a guide track 120, a carriage 122, and opposing, first and second legs 124, 126. In general terms, the legs 124, 126 maintain the guide track 120 relative to the PS transmission sub-assembly 70. The carriage 122 supports a motor M2 relative to the guide track 120. The handle 44 is coupled to the carriage 122, for example via an optional rail 128. With this construction, the motor operates to articulate the carriage 122 (and thus the handle 44) along the guide track 120.

The guide track 120 is sized and shaped to establish a desired path of travel for the carriage 122, and in some embodiments approximates a semi-circle (or U-shape). Other shapes, and thus other paths of travel, are envisioned that may include curved segments presenting two or more differing radii of curvature, curvilinear segments, linear segments, etc. With embodiments in which the shape of the guide track 120 is a semi-circle (or other shape having a single radius of curvature), a centerline of the so-generated shape establishes an FE axis of the manipulandum unit 22 and about which the carriage 122 (and thus the handle 44) articulates. The guide track 120 incorporates one or more coupling features appropriate for interfacing with an output shaft of the motor M2 mounted to the carriage 122, for example a slot 130. In some embodiments, an optional support track 132 is provided, having a size and shape approximating that of the guide track 120. The support track 132 is configured to reinforce the guide track 120 and promote a more robust coupling of the guide track 120 with the legs 124, 126.

The carriage 122 can assume various forms appropriate for maintaining the motor (not shown), and in particular ensuring an engaged interface between an output shaft of the motor and the corresponding coupling feature (e.g. the slot 130) of the guide track 120. In some embodiments, the carriage 122 includes opposing housing sections 140, 142 configured for mated assembly, and one or more optional bearings 144 (visible in FIG. 5). The bearings 144 are rotatably disposed within the housing sections 140, 142, and promote smooth movement or articulation of the carriage 122 (and the motor) along a shape of the guide track 120.

The handle 44 can be attached to the carriage 122 in various fashions. For example, in some embodiments, the handle 44 can be directly mounted or fixed to the carriage 122. In other embodiments, the FE transmission sub-assembly 72 can be configured such that handle 44 is connected to the carriage 122 in a manner permitting selective re-positioning of the handle 44. For example, the rail 128 can be interposed between the handle 44 and the carriage 122. The rail 128 is an elongated body adapted for mounted assembly to the carriage 122 (e.g., to the upper housing section 140). A slide body 150 is disposed along the rail 128, and is configured for coupling with the handle 44 (e.g., via a foot 152 provided with the handle 44). The slide body 150 can establish a frictional-type engagement with the rail 128, but can be slid or articulated along a length of the rail 128 when subjected to sufficient external force. In other words, the slide body 150 does not freely slide along the rail 128, but instead will self-maintain a selected position relative to the rail 128 unless subjected to an overt force. Upon final assembly, the slide body 150, and thus the handle 44, can be selectively re-positioned or adjusted along a length of the rail 128 as desired. This adjustable arrangement promotes use of the manipulandum unit 22 properly scaled to a subject's anthropometrics (e.g., differences in forearm length between an adult and a child; adult subjects may prefer to locate the handle 44 at a greater distance from the carriage 122 as compared to child subjects). Optional stops 154 can be assembled to opposite ends of the rail 128 to prevent the slide body 150 from inadvertently sliding off of the rail 128.

The legs 124, 126 can be substantially identical in some embodiments (e.g., mirror images), and are generally sized and shaped for assembly to the guide track 120 and for connection with a corresponding one of the PS transmission sub-assembly arms 82, 84. As identified for the first leg 124, each of the legs 124, 126 can include or define a leg body 160 terminating at or forming a head 162. The head 162 is configured to facilitate a pivotable or hinged connection with a corresponding component of the PS transmission sub-assembly 70. For example, the head 162 can include or form a bore 164 sized and shaped to rotatably receive a pin, shaft or other mounting body (not shown). Other mounting techniques are also acceptable. Regardless, upon final assembly the common AA axis as described above is established at the head 162 of the legs 124, 126 and about which the FE transmission sub-assembly 72 can pivot relative to the PS transmission sub-assembly 70 as described below.

Upon final assembly, and as reflected in FIGS. 2A and 2B, the PS transmission sub-assembly 70 and the FE transmission sub-assembly 72 are linked to one another at corresponding pairs of the arms 82, 84 and legs 124, 126. In particular, the first arm 82 is connected to the first leg 124, and the second arm 84 is connected to the second leg 126. The connection format can assume various forms capable of establishing a pivotable relationship between the arms 82, 84 and the legs 124, 126. For example, and as alluded to above, a pin or similar body (not shown) can be provided at each arm/leg interface that connects the arm 82, 84 with the corresponding leg 124, 126 in a manner permitting rotation of the leg 124, 126 relative to the corresponding arm 82, 84 about the pin. Regardless of exact form, the FE transmission sub-assembly 72 is pivotable relative to the transmission sub-assembly 70 about the AA axis.

Figure 6A:
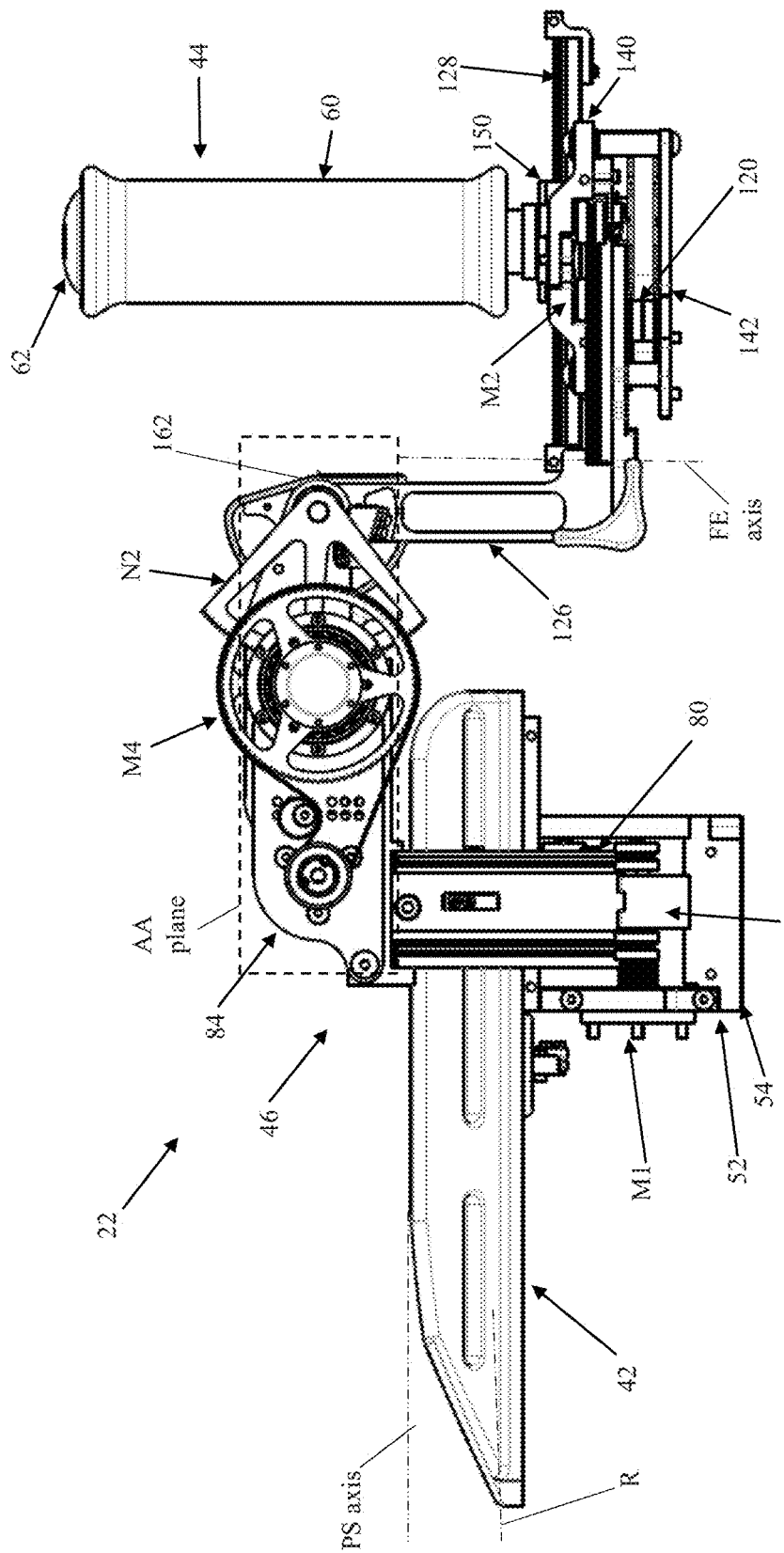
FIG. 6A is a side view of the manipulandum unit of FIG. 2A.
Figure 6B:
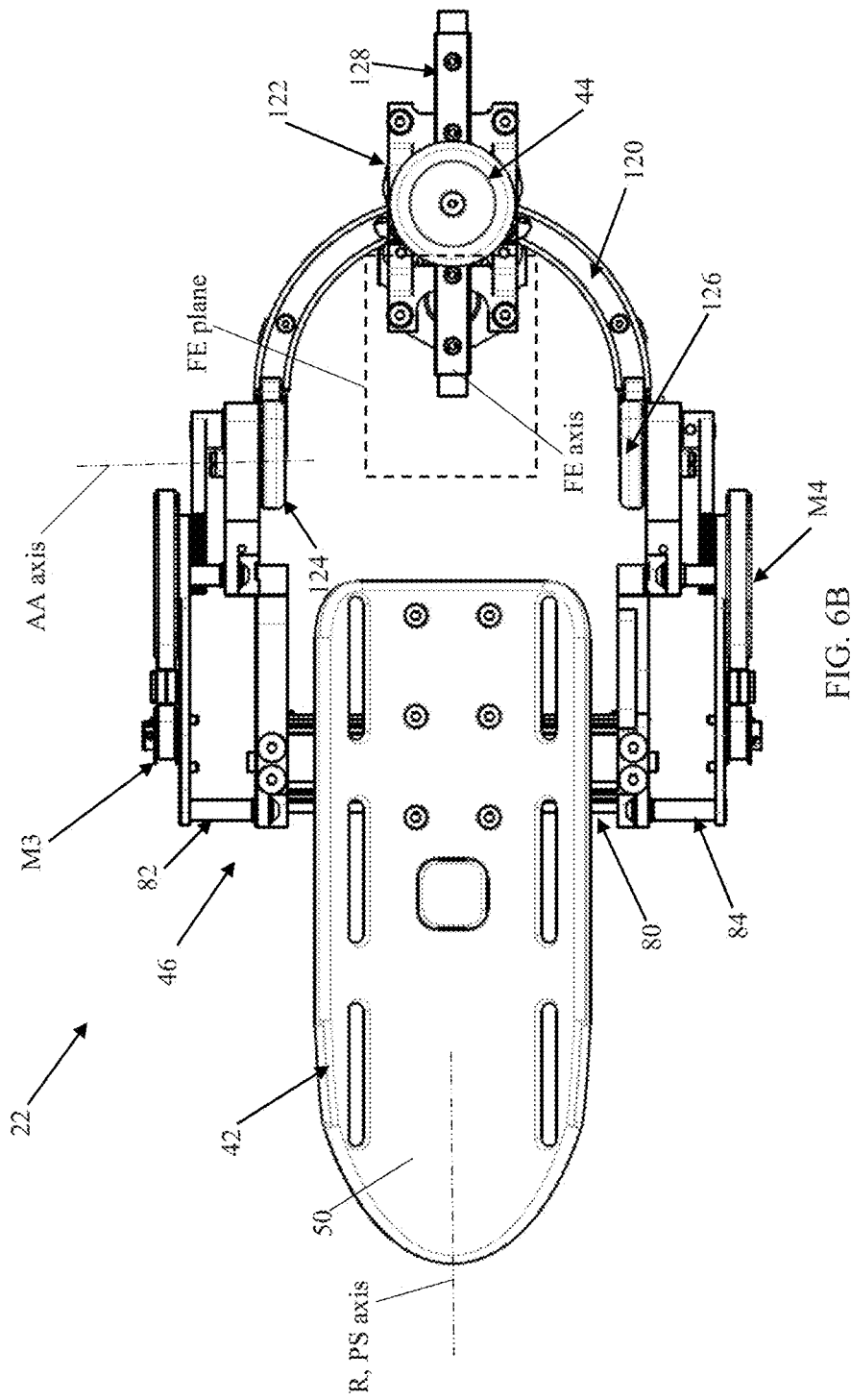
FIG. 6B is a top view of the manipulandum unit of FIG. 2A.
Figure 6C:
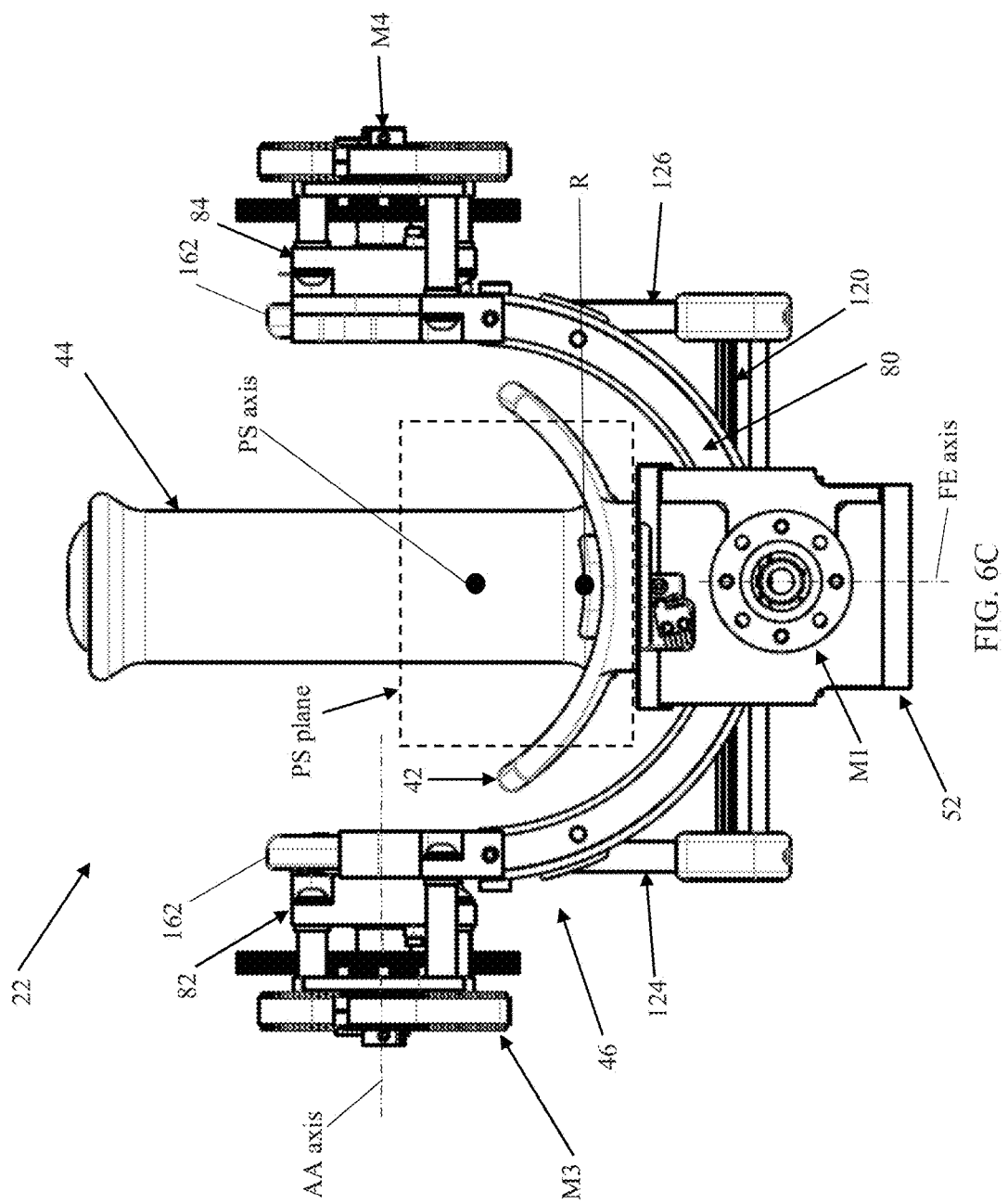
FIG. 6C is a rear view of the manipulandum unit of FIG. 2A.

With additional reference to FIGS. 6A-6C, the linkage assembly 46 permits movement of the handle 44 relative to the base 42 with three DOF in which the handle 44 can be articulate about three axes. The three axes or DOF can be designated with reference to anatomical movements of the human wrist joint when manipulated by the unit 22. As identified in FIGS. 6A-6C, the connection between the arms 82, 84 and the legs 124, 126 permits pivoting or articulation of the handle 44 relative to the base 42 about the AA axis that otherwise induces with abduction-adduction movement of the wrist joint in a sagittal or AA plane of the unit 22. The connection between the handle 44 and the guide track 120 (via the carriage 122) permits pivoting or articulation of the handle 44 relative to the base 42 about an FE axis of the unit 22 that otherwise induces flexion-extension movement of the wrist joint in a transverse or FE plane of the unit 22. Finally, the connection between the track 80 and the base 42 permits pivoting or articulation of the handle 44 relative to the base 42 about a PS axis of the unit 22 that otherwise induces pronation-supination movement the subject's hand in a PS plane of the unit 22. The AA, FE, and PS axes have prescribed relationships relative to one another and relative to the reference axis R of the base 42 so as to ergonomically coincide with anatomical movements of a subject's wrist joint and hand when the forearm rests on the base 42 and the hand grasps the handle 44. For example, the PS axis is substantially parallel (e.g., within 5 degrees of a truly parallel relationship) with the reference axis R. The FE axis is substantially perpendicular to (e.g., within 5 degrees of a truly perpendicular relationship) the PS axis and to the reference axis R. Finally, the AA axis is substantially perpendicular to (e.g., within 5 degrees of a truly perpendicular relationship) the FE axis and the PS axis (and thus also the reference axis R). It has surprisingly been found that the non-limiting example of the manipulandum unit 40 as described above provides a range of motion (ROM) of the three DOFs that substantially matches the ROM of an adult human wrist. For example, some embodiments of the manipulandum units of the present disclosure have a ROM about the FE axis of +−72 degrees; about the AA axis of 45 degrees/27 degrees; about the PS axis of +−80 degrees. By way of comparison, the human wrist joint typically presents a ROM in flexion/extension of 65 degrees/70 degrees; in abduction/adduction of 15 degrees/30 degrees; in pronation/supination of +−90 degrees.

As mentioned above, the manipulandum unit 22 includes one or more motors M1-M4 interfacing with the linkage assembly 46, and in particular controlling or dictating a stationary spatial position of the handle 44 relative to the base 42 as well as movement of the handle 44 about each of the AA, FE, and PS axes. In some embodiments, a first motor (not shown, but a possible location of which is referenced in the Figures at "M1") is operably associated with the track 80, for example by assembly to the carrier 52. The first motor M1 can take various forms, and is generally configured such that an output shaft of the first motor M1 is coupled to the track 80, with movement (e.g., rotation) of the first motor M1 output shaft causing the track 80 to articulate (i.e., during operation, the first motor M1 remains stationary while the track 80 is actuated to move). Commensurate with previous explanations, then, operation of the first motor M1 corresponds with movement of the handle 44 relative to the base 42 about the PS axis. Further, the first motor M1 and the first motor M1/track 80 interface is configured such that the first motor M1 resists or prevents movement of the track 80 when the output shaft of the first motor M1 is not rotationally driven. In other words, the first motor M1 serves to dictate and maintain a spatial position of the handle 44 in the PS plane of the manipulandum unit 22.

The second motor M2 is operably associated with the guide track 120, for example by assembly to the carriage 122. The second motor M2 can take various forms, and is generally configured such that an output shaft of the second motor M2 is coupled to the guide track 120, with movement (e.g., rotation) of the second motor M2 output shaft causing the second motor M2 (and thus the carriage 122 and the handle 44) to articulate along or relative to the guide track 120 (i.e., during operation, the guide track 120 remains stationary while the second motor M2 (and handle 44) is actuated to move). Commensurate with previous explanations, then, operation of the second motor M2 corresponds with movement of the handle 44 relative to the base 42 about the FE axis. Further, the second motor M2 and the second motor M2/guide track 120 interface is configured such that the second motor M2 resists or prevents movement of the second motor M2 relative to the guide track 120 when the output shaft of the second motor M2 is not rotationally driven. In other words, the second motor M2 serves to dictate and maintain a spatial position of the handle 44 in the FE plane of the manipulandum unit 22.

The third motor M3 is operably associated with the pivotable connection between the first arm 82 and the first leg 124. The fourth motor M4 is operably associated with the pivotable connection between the second arm 84 and the second leg 126. Transmission to the leg 126 can be obtained by a geared mechanism N1, N2 including pulleys, a belt and pinion or the like. The third and fourth motors M3, M4 can take various forms. The third motor M3 is generally configured such that an output shaft of the third motor M3 is coupled (directly or indirectly) to the head 162 of the first leg 124, with movement (e.g., rotation) of the third motor M3 output shaft causing the first leg 124 to articulate or pivot relative to the first arm 82 (i.e., during operation of the third motor M3, the first arm 82 remains stationary while the first leg 124 is actuated to move). Coupling of the third motor M3 with the first leg 124 can be achieved in various manners, and in some embodiments can entail a gear G, belt B and pulley P type arrangement (see, in particular, FIG. 4). A similar relationship can be provided between the fourth motor M4 relative to the second leg 126. The third and fourth motors M3, M4 can be operated in tandem. Commensurate with previous explanations, then, operation of the third and fourth motors M3, M4 corresponds with movement of the handle 44 relative to the base 42 about the AA axis. Further, the third and fourth motors M3, M4 and the corresponding interfaces with the legs 124, 126 is configured such that the third and fourth motors M3, M4 resist or prevent movement of the legs 124, 126 (and thus the handle 44) relative to the arms 82, 84 when the output shaft of the third and fourth motors M3, M4 are not rotationally driven. In other words, the third and fourth motors M3, M4 serve to dictate and maintain a spatial position of the handle 44 in the AA plane of the manipulandum unit 22.

In some embodiments, the motors M1-M4 are brushless motors selected to provide an accurate haptic rendering and provide sufficient force to stabilize a human wrist against gravity and/or overcome expected or possible muscular forces of a subject (e.g., due to hypertonia (rigidity) or spasticity). In one non-limiting embodiment, the manipulandum unit 22 (via a construction of the linkage assembly 46 and the selected motors M1-M4) is configured to provide maximum torque values in the three DOFs on the order of 1.53 Nm with respect to the FE axis, 1.63 Nm with respect to the AA axis, and 2.77 Nm with respect to the PS axis. Other configurations are also envisioned, and in other embodiments more or less than four of the motors M1-M4 can be included.

Returning to FIG. 1, in some embodiments the controller 24 includes a computing system or computing device that includes at least one processor and memory. Depending on the exact configuration and type of computing device, the memory may be volatile (such as RAM), non-volatile (such as ROM, flash memory, etc.), or some combination of the two. The memory used by the controller 24 is an example of computer storage media (e.g., non-transitory computer-readable storage media storing computer-executable instructions for performing a method). Computer storage media used by the controller 24 according to some embodiments includes volatile and nonvolatile, removable and non-removable media implemented in any suitable method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by the controller 24.

Regardless of exact form, and with additional reference to FIGS. 2A and 2B, the controller 24 is configured or programed to control operation of, and receive (and optionally act upon) information or data generated at, the motor(s) M1-M4 provided with the manipulandum unit 22. For example, in some embodiments an angular position or rotation on the three axes (AA axis, FE axis, PS axis) of the manipulandum unit 22 are measured by means 23 of a rotary encoder provided with each of the motors M1-M4. Rotary encoders are known in the art, and operate to convert the angular position of motion of the motor's output shaft to a digital or analog code that in turn is indicative of the angular position or rotation relative to the axis to which the motor M1-M4 is associated. The rotary encoders can assume a variety of forms (e.g., digital or analog, absolute or incremental), and in some embodiments are digital incremental encoders with a resolution of 4098 bits/turn or 2048 bits/turn.

The controller 24 incorporates appropriate input/output modules for interfacing (e.g., wired or wirelessly) with the manipulandum unit 22, the display(s) 26, and any other equipment provided with the system 20 over which control is desired. For example, the controller 24 can include an analog and digital I/O PCI card (available from Sensoray under the trade designation "Model 626"). The input/output module(s) can provide multiple interface channels, for example four 14 bit D/A channels for commanding the reference values of the currents of the motors M1-M4, and four 24-bit counters for receiving the repetition signals of the digital encoders. For example, the controller 24 can be connected through an Ethernet interface directly with motor control cards used for commanding the reference values of the currents of the motors M1-M4 and for receiving signals of the digital encoders. Any other interface format known to those of ordinary skill are also acceptable.

As described in greater detail below, the controller 24 is programmed (e.g., software or stored in memory) actuate the manipulandum unit 22 (i.e., actuate selective ones of the motors M1-M4 that in act upon the linkage assembly 46 to manipulate the handle 44 relative to the base 42) to perform various, pre-determined operations, such as proprioception assessment and/or rehabilitation operations. Further, the controller 24 can prompt operation of the display 26 (where provided) in connection with one or more of the predetermined operations. With this in mind, the controller 24 can include a control architecture for effectuating performance of the pre-determined operations, such as a control architecture based on three loops: 1) an inner loop, for example running at 1 kHz, 7 kHz or 20 kHz, for controlling the motor servos; 2) an intermediate loop, for example running at 1 kHz on a real time kernel, that updates the current reference of each motor; 3) an external loop, for example running at 100 Hz, for a visual virtual reality generated at the display 26 (or other user interface).

Figure 7:
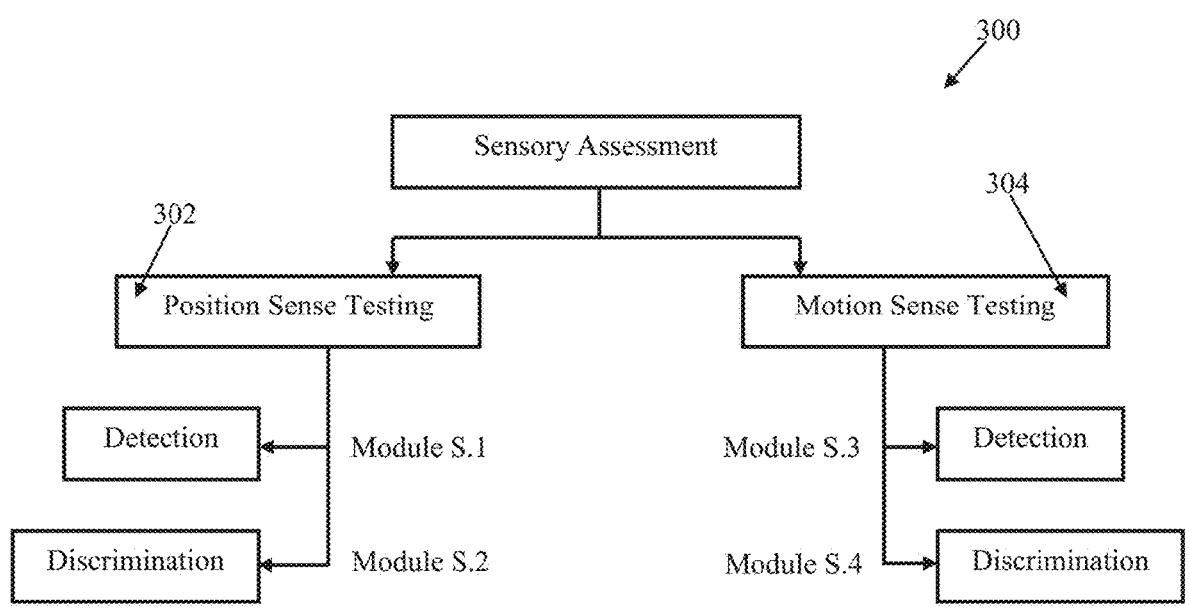
FIG. 7 is a block diagram of a sensory assessment program useful with the system of FIG. 1.

The controller 24 can be configured or programmed (e.g., software) to perform various proprioception-related operations, including an assessment program and an optionally rehabilitation or training program, that can be independently selected by the subject or clinician. One embodiment of a proprioception or sensory assessment program 300 useful with the present disclosure is shown in block form in FIG. 7. The assessment program 300 includes a plurality of individual routines or modules that can be categorized based upon related subject matter. For example, the assessment program 300 can include a Position Sense category 302 and a Motion Sense category 304. The phrase "position sense" refers to a subject's ability to perceive the position of his/her wrist. The phrase "motion sense" refers to the subject's ability to perceive motion around the wrist joint. Under each category, one or more independent modules or routines are available for selection by the subject or clinician and that each objectively tests one aspect of proprioceptive function. The individual modules or routines can be written in any acceptable programming language known in the art (e.g., Matlab Simulink Technical Programming Language, C++ or Python). The routines are premised upon a subject's interface with the manipulandum unit 22 as generally reflected by FIG. 8. The handle 44 is grasped by the subject's hand H, while the subject's forearm F rests on the base 42. A frontal plane of the subject is generally aligned perpendicular to the PS axis (FIG. 6A) of the manipulandum unit 22, and the subject's wrist W naturally assumes a neutral joint position. Though not shown, in some embodiments, a strap or similar device can be employed to more firmly secure the subject's forearm to the base 42. Finally, in some embodiments the routines of the assessment program 300 (FIG. 7) can generate more reliable results where the subject's vision is occluded (e.g., opaque glasses) and the subject's hearing is masked (e.g., noise-cancelling headphones) to eliminate possible visual or acoustic cues.

Figure 9A:
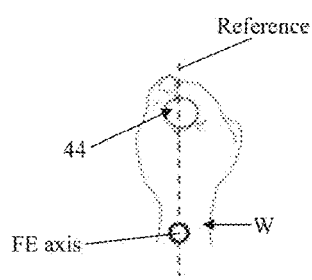
FIGS. 9A-9C illustrate flexion-extension articulation of a subject's wrist joint by the systems of the present disclosure.
Figure 9B:
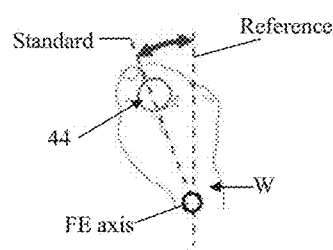
Figure 9C:
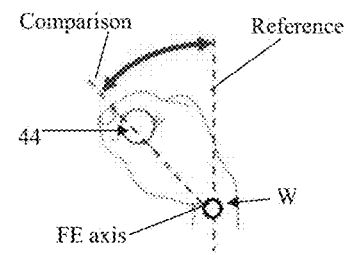
Figure 10A:
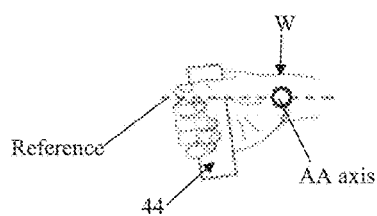
FIGS. 10A-10C illustrate abduction-adduction articulation of a subject's wrist joint by the systems of the present disclosure.
Figure 10B:
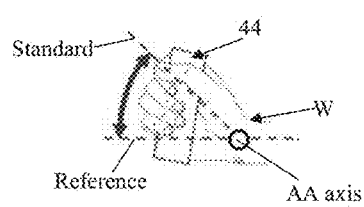
Figure 10C:
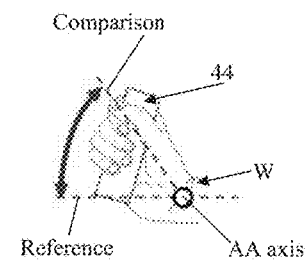

Returning to FIG. 7, the Position Sense category 302 can include a Position Sense Detection Module S.1. The Position Sense Detection Module S.1 is generally programmed to indicate the minimum change in wrist position that a subject is able to perceive. The Position Sense Detection Module S.1 can be programmed to assess the subject's position sense detection threshold in each of the three DOFs available with the manipulandum unit 22. For example, FIG. 9A reflects a reference position of the subject's wrist joint W relative to the transverse or FE plane of the manipulandum unit 22. The FE axis is also identified. The Position Sense Detection Module S.1 can be programmed to use the reference position as a starting point, and then prompt the manipulandum unit 22 (FIG. 2A) to articulate the handle 44, and thus the subject's wrist joint W, about the FE axis to one or more pre-determined positions. For example, FIG. 9B reflects movement of the handle 44 (in the transverse plane) to a first or standard position, causing the subject's wrist joint W to experience flexion. Under some scenarios, the Position Sense Detection Module S.1 is programmed to temporarily hold the handle 44 (and thus the subject's wrist joint W) in the standard position to allow the subject to provide an indication as to whether or not s/he perceives a change from the reference position (e.g., the subject can provide a clinician with a verbal statement indicating whether or not s/he has perceived a change in position, with this indication be recorded (in writing or electronically)). After a certain amount of time and/or in response to a clinician's prompt, the Position Sense Detection Module S.1 is programmed to return the handle 44 back to the reference position. This process can be repeated for a multitude of different positions about the FE axis, with the collective results providing an objective assessment of the subject's proprioceptive function about the FE axis. For example, FIG. 9C reflects movement of the handle 44, and thus the subject's wrist joint W, to a different or first comparison position. Response(s) (or lack thereof) by the subject to perceived changes in the wrist joint W at the standard position and the first comparison position (as well as many other positions about the FE axis) can be informative. Similar assessments can be performed relative to the AA axis (as represented, for example, by FIGS. 10A-10C) and the PS axis of the manipulandum unit 22. Upon completion of the Position Sense Detection Module S.1 testing, the results can be compared against standardized results of others under identical testing conditions and/or saved for comparison with the results of a subsequent Position Sense Detection Module S.1 testing for the same subject (e.g., following a rehabilitation program to better identify or recognize improvements in proprioceptive function).

Returning to FIG. 7, the Position Sense category 302 can also include a Position Sense Discrimination Module or routine S.2. The Position Sense Discrimination Module S.1 is generally programmed to indicate the smallest noticeable difference in two wrist arrangements that a subject is able to perceive. The Position Sense Discrimination Module S.2 can be programmed to assess the subject's position sense discrimination threshold in each of the three DOFs available with the manipulandum unit 22 (FIG. 2A). The Position Sense Discrimination Module S.2 can be programmed to actuate the manipulandum unit 22 in manners akin to the descriptions above with respect to the Position Sense Detect Module S.1, causing the subject's hand to move (articulating the wrist joint) about the corresponding axis of interest to a number of different pre-determined positions. With the Position Sense Discrimination Module S.2, however, the user's wrist joint may be caused to move incrementally between various pre-determined positions and need not necessarily return to the reference position.

The Motion Sense category 304 can include a Motion Sense Detection Module or routine S.3. The Motion Sense Detection Module S.3 is generally programmed to indicate the minimum rate of motion at the wrist joint that a subject is able to perceive. The Motion Sense Detection Module S.1 can be programmed to assess the subject's motion sense detection threshold in each of the three DOFs available with the manipulandum unit 22 (FIG. 2A). The Motion Sense Detection Module S.3 can be programmed to actuate the manipulandum unit 22 in manners akin to the descriptions above with respect to the Position Sense Detect Module S.1, causing the subject's hand to move (articulating the wrist joint) in the corresponding axis of interest from the reference position to a pre-determined position(s), and then back to the reference position, at different rates or speeds. After (or during) each cycle, the subject can be prompted to indicate whether or not s/he perceives any motion in his/her wrist joint and/or the "level" or amplitude of motion.

The Motion Sense category 304 can also include a Motion Sense Discrimination Module or routine S.4. The Motion Sense Discrimination Module S.4 is generally programmed to indicate the smallest noticeable difference in two different rates or speed of motion at the wrist joint that a subject is able to perceive. The Motion Sense Discrimination Module S.4 can be programmed to assess the subject's motion sense discrimination threshold in each of the three DOFs available with the manipulandum unit 22 (FIG. 2A). The Motion Sense Discrimination Module S.4 can be programmed to actuate the manipulandum unit 22 in manners akin to the descriptions above with respect to the Position Sense Detect Module S.1, causing the subject's hand to move (in turn articulating the wrist) about the corresponding axis of interest at a number of different pre-determined rates or speeds. The subject can be prompted to indicate which of two (or more) different movement cycles was "faster" than the others.

Other sensory assessment modules or routines can be provided with the treatment systems of the present disclosure. By providing objective tests of different aspects of proprioceptive function, an overall, objective assessment of sensory dysfunction at the subject's wrist joint is provided.

Figure 11:
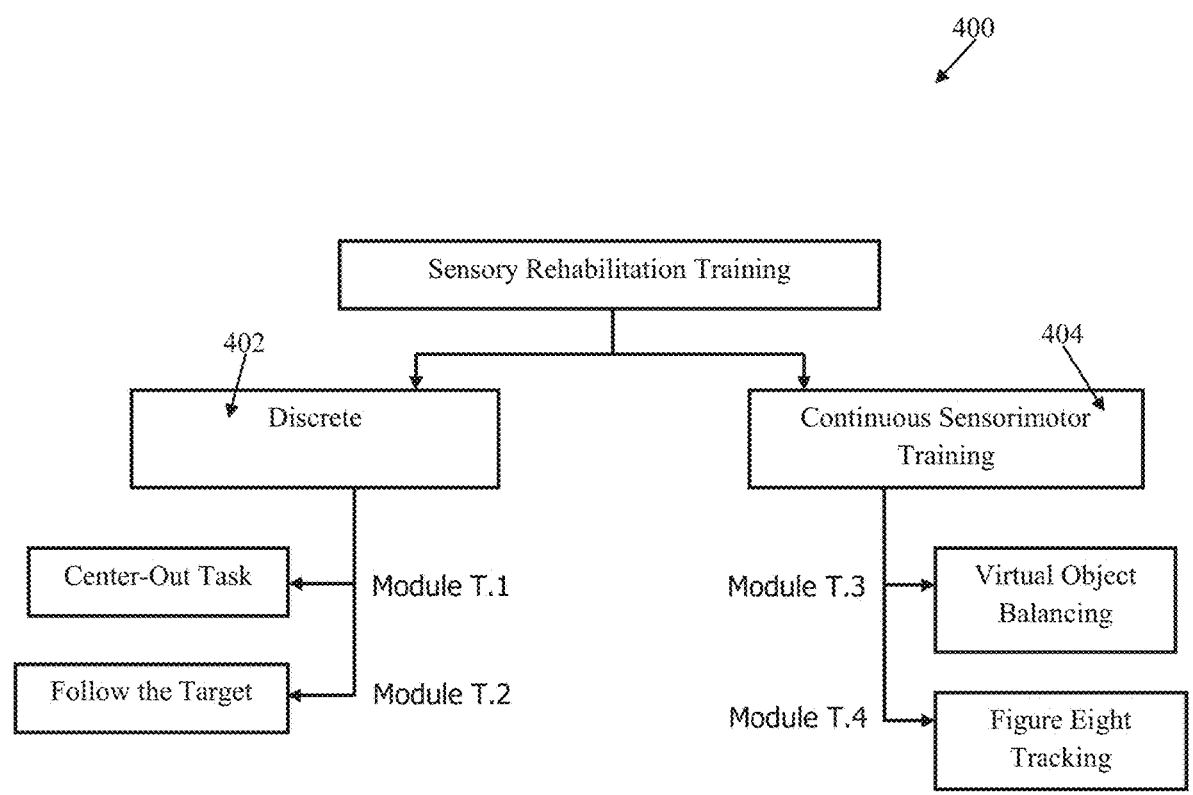
FIG. 11 is a block diagram of a sensory rehabilitation training program useful with the systems of the present disclosure.

In addition to assessment, the systems of the present disclosure are optionally configured to perform automated proprioceptive function training or rehabilitation on a subject, via software or other programming provided with the controller 24 (FIG. 1). One embodiment of a proprioception or sensory rehabilitation training program 400 useful with the present disclosure is shown in block form in FIG. 11. The rehabilitation training program 400 includes a plurality of individual routines or modules that can be categorized based upon related subject matter. For example, the rehabilitation training program 400 can include a Discrete category 402 and a Continuous Sensorimotor Training category 404. The term "discrete" refers to goal-directed wrist movements from point A to point B. The phrase "continuous sensorimotor training" refers to continuous movements (i.e., those that do not have a defined spatial or temporal end). Under each category, one or more independent modules or routines are available for selection by the subject or clinician, and that are designed to improve proprioceptive and sensorimotor function. The individual modules or routines can be written in any acceptable programming language known in the art (e.g., Matlab Simulink Technical Programming Language, C++ or Phython). The routines are premised upon a subject's interface with the manipulandum unit 22 as generally reflected by FIG. 8 and as described above. However, for some phases of training, the subject's vision may not be occluded. For example, at the beginning of the training, the subject is provided with visual feedback though the use of the display 26 (FIG. 1) or other virtual reality tools, prompting the subject to interface with the manipulandum unit 22 in controlling certain items or objects as shown on the display 26. More particularly, the controller 24 operates (per the selected routine) to generate a virtual reality environment on the display 26, with the virtually reality environment including at least one virtual object that can "move" on or within the display 26 in response to movements at the manipulandum unit 22 (as otherwise controlled by the subject). The controller 24 is programmed to correlate movements at the manipulandum unit 22 on to the display 26. In subsequent phases of training, subjects may perform movements without vision, for example relying solely on memory or may receive additional vibro-tactile feedback during movement execution through vibromotors tipically attached to the skin of the forearm or any other suitable bodily surface.

The Discrete category 402 can include a Center-Out Task module T.1. The Center-Out Task module T.1 is generally programmed to present, on the display 26, a virtual or neural cursor that is controlled by the subject (via the manipulandum unit 22) along with a virtual target. The target is randomly located on the display 26, and the goal is for the subject to move the virtual cursor over the target and then "hold" the virtual cursor over the target for a pre-determined length of time. The Center-Out Task module T.1 can be configured to require subject control over the virtual cursor in one, two or all three of the movement axes or planes of the manipulandum unit 22 (i.e., AA axis, FE axis and/or PS axis). Further, the level of difficulty can be increased as the subject becomes increasingly competent in performing or solving the presented task.

The Discrete category 402 can include a Follow the Target module T.2. The Follow the Target module T.2 is generally programmed to present, on the display 26, a virtual or neural cursor that is controlled by the subject (via the manipulandum unit 22) along with a virtual target. The target is randomly moved on the display 26 from a first point to a second point, and the goal is for the subject to move the virtual cursor with the moving target. The Follow the Target module T.2 can be configured to require subject control over the virtual cursor in one, two or all three of the movement axes or planes of the manipulandum unit 22 (i.e., AA axis, FE axis and/or PS axis). Further, the level of difficulty can be increased as the subject becomes increasingly competent in performing or solving the presented task.

The Continuous Sensorimotor Training category 404 can include a Virtual Object Balancing module T.3. The Virtual Object Balancing module T.3 is generally programmed to present, on the display 26, a small virtual ball on a tiltable surface that is controlled by the subject (via the manipulandum unit 22). The goal is for the subject to keep the ball on the surface. The Virtual Object Balancing module T.3 can be configured to require subject control over the virtual cursor in one, two or all three of the movement axes or planes of the manipulandum unit 22 (i.e., AA axis, FE axis and/or PS axis). Further, the level of difficulty can be increased as the subject becomes increasingly competent in performing or solving the presented task.

The Continuous Sensorimotor Training category 404 can include a Figure Eight Tracking module T.4. The Figure Eight Tracking module T.4 is generally programmed to present, on the display 26, a pattern in the shape of a FIG. 8, along with a virtual or neural cursor that is controlled by the subject (via the manipulandum unit 22). The goal is for the subject to manipulate the virtual cursor within the FIG. 8 pattern. Further, the level of difficulty can be increased as the subject becomes increasingly competent in performing or solving the presented task.

Other sensory rehabilitation training modules or routines can be provided with the treatment systems of the present disclosure. By integrating assessment and training into a single, automated system, proprioceptive function of a subject in 3 DOFs can be repeatedly assessed and trained, providing the clinician with an objective understanding of the subject's progress.

EXAMPLES

To confirm the viability of objective proprioceptive function assessment with systems of the present disclosure, experiment sessions were performed on subjects using a manipulandum unit akin to that shown and described above with respect to FIGS. 2A and 2B. The manipulandum unit provided three DOFs, and was powered by four brushless motors collectively providing continuous torque ranges at the wrist joint of 1.53 Nm at the FE axis, 1.63 Nm at the AA axis, and 2.77 Nm on the PS axis. Angular rotations on the three axes were acquired by means of 4000 quadrature-counts/revolution incremental encoders, resulting in a resolution of 0.0075° for FE DOF and 0.0032° for AA DOF. The manipulandum unit was electronically connected to and controlled by a controller that also operated a visual virtual reality environment. The controller utilized a three control loop control architecture: 1) an inner loop, running at in the motor servos; 2) an intermediate loop, running at 1 kHz, on a real time kernel that updates the current reference of each motor; 3) an external loop, running at 100 Hz, for the visual virtual reality and user interface. The gain parameters of the PID controller running inside the motor drivers were tuned to delivery smooth movements desirable for the psychophysical threshold determination tests described below.

Eleven right-handed young adults with no known neurological and neuromuscular disorders, (mean age±SD: 26.4±3.4 yrs.) volunteered to participate in the study. The Edinburgh Handedness Questionnaire was administered to determine handedness. All participants revealed a laterality index of >60 on a [−100 100] scale (mean±SD: 82.7±12.9), where −100 means completely left-handed and 100 completely right-handed, showing that they were right-hand dominant. Only the dominant right hand was evaluated.

Figure 8:
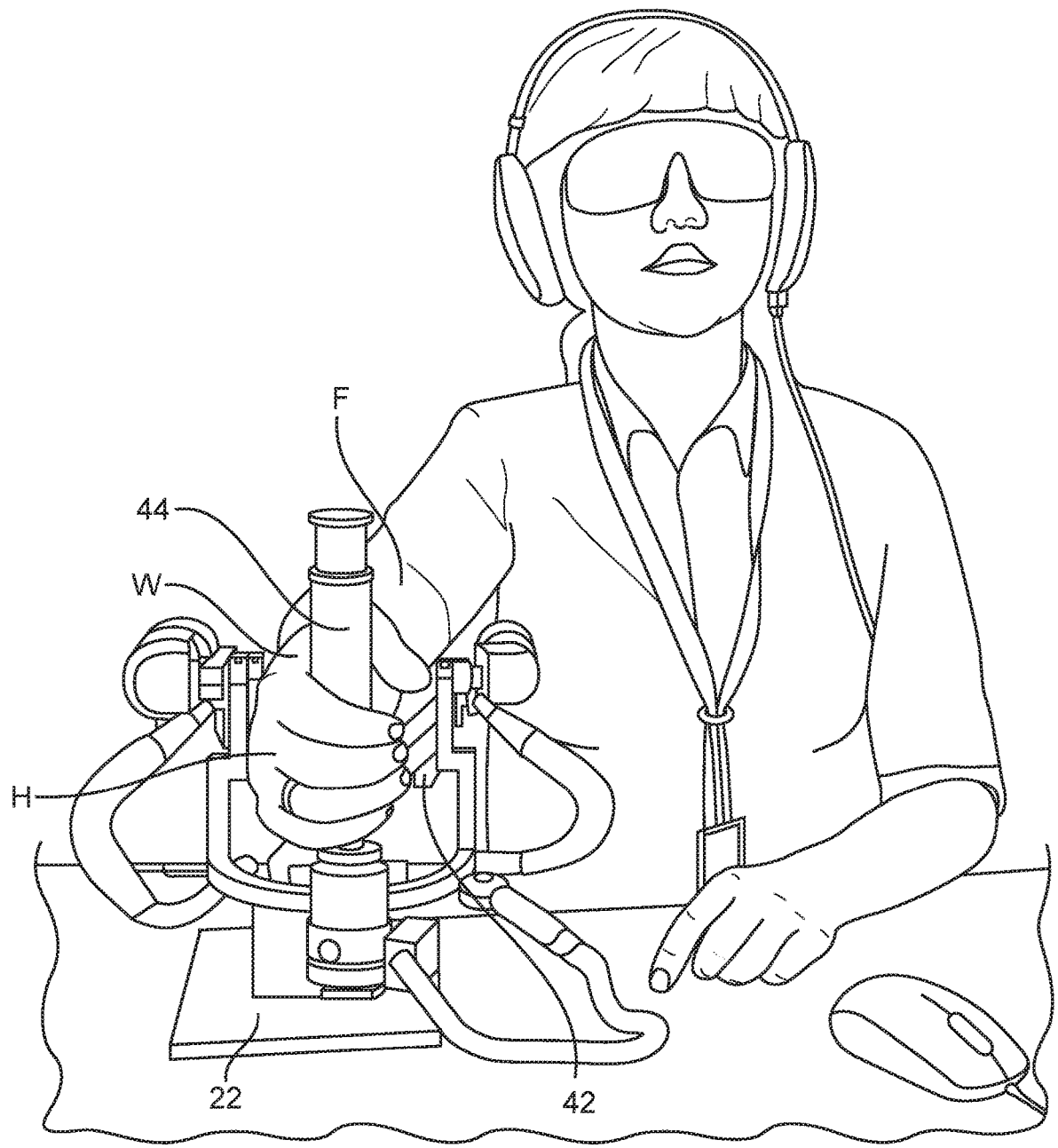
FIG. 8 is a simplified illustration of a subject interfacing with the manipulandum unit of FIG. 2A.

Subjects sat next to the manipulandum unit (akin to the representation of FIG. 8). The frontal plane of the body was aligned perpendicularly to the PS axis of the manipulandum unit, which is horizontal. Seat position was adjusted in order to be comfortable for the participants, with the elbow angle of ~90°. Particular attention was given to the correct alignment of the wrist joint with the functional axis of the manipulandum unit: to avoid joint misalignment and unwanted relative movements between the wrist and the manipulandum unit during the experiment, the subject's forearm was firmly constrained to the base and secured by Velcro@ strips. Subjects were instructed to maintain a relaxed hand grip. Prior to testing the wrist assumed a neutral joint position during FE condition, while in AA condition the joint was adducted by 10° from neutral in order to prevent the manipulandum unit from reaching the anatomical limit of the workspace during stimulus presentation.

Figure 12:
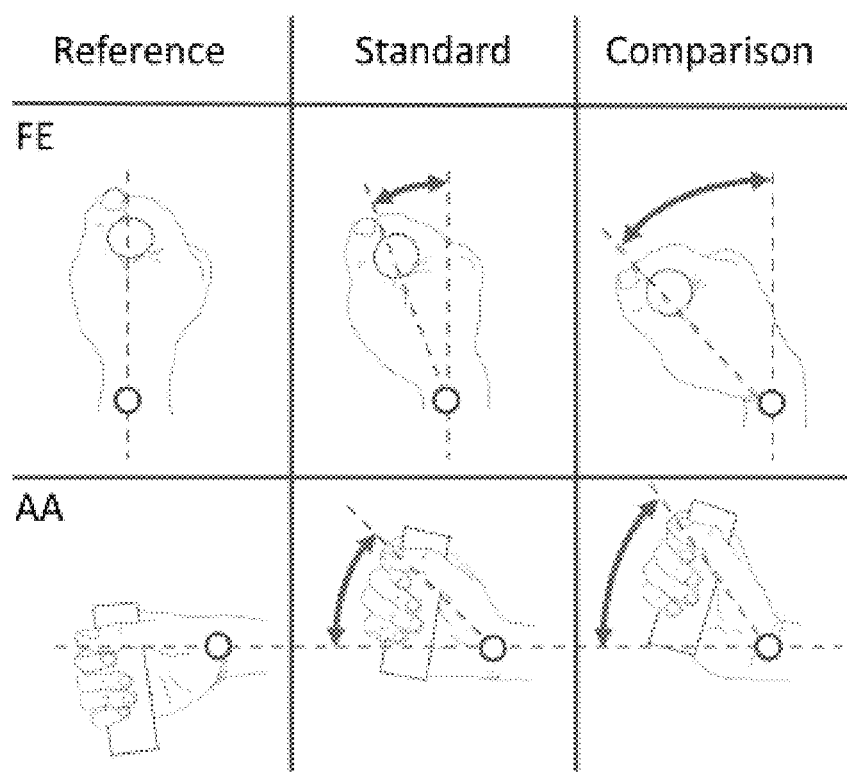
FIG. 12 illustrates displacement of a subject's wrist joint as described in the Examples.

Vision was occluded by opaque glasses and hearing was masked by noise-cancelling headphones to eliminate possible visual or acoustic cues. A unidirectional 2-alternative-forced-choice (2AFC) discrimination paradigm was chosen. Two different stimuli were presented in each trial: a 15° amplitude stimulus of fixed value (standard stimulus) and the other with variable amplitude across trials (comparison stimulus) and always higher than the standard as represented in FIG. 12). The term "intensity" was referred to as the difference between the angular displacement of the two standard and comparison stimuli. The two stimuli were presented in random order, separated by a 2-second inter-stimulus interval. After each trial, the subject verbally indicated which stimulus was "larger" (i.e. which of the two movements had a larger displacement). Based on the subject's response, a comparison stimulus was selected for the subsequent trial using an adaptive QUEST algorithm developed by Watson & Pelli. In order to provide the subject with a more heterogeneous task, a random Gaussian noise was added for every trial to the comparison stimulus set to a maximum of ±20% of the current comparison stimulus itself. During each trial the velocity of movement was kept constant at 6°/s.

The two conditions were tested separately: each session lasted for approximately 45 minutes with 3 minutes rest after every 15-25 trials in order to prevent mental fatigue and enhance attention, a prerequisite for the validity of obtained psychophysical thresholds. The intensity of the first trial was set to 7° in order to be easily detectable by all the subjects.

To obtain a proprioceptive threshold, the frequency of correct responses where the comparison stimulus was identified as larger than the standard stimulus was computed across the range of displayed stimuli. Response data were then fitted using a cumulative Gaussian function. A psychometric acuity function $\Psi$ was computed for both the conditions, where $\Psi$ describes the probability that a comparison at x is picked as the stimulus with the larger intensity. The psychometric function ranges from 50% to 100%. This implies that for low stimulus intensities the subject had a 50% of probability to give the correct answer, while for large intensities the comparison was correctly perceived as larger in 100% of trials. Based on $\Psi$, a discrimination threshold was defined as the intensity such that the subjects identified the comparison as larger with a frequency of 75%.

Figure 13:
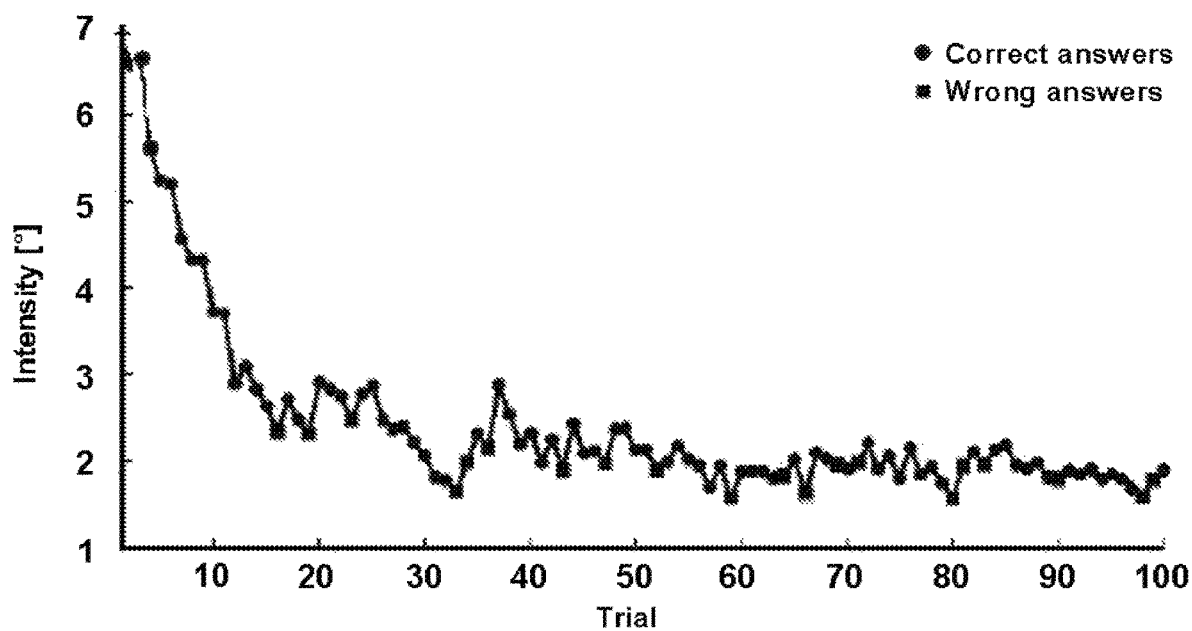
FIG. 13 is a graph showing the testing results of a subject of the testing described in the Examples section.
Figure 14:
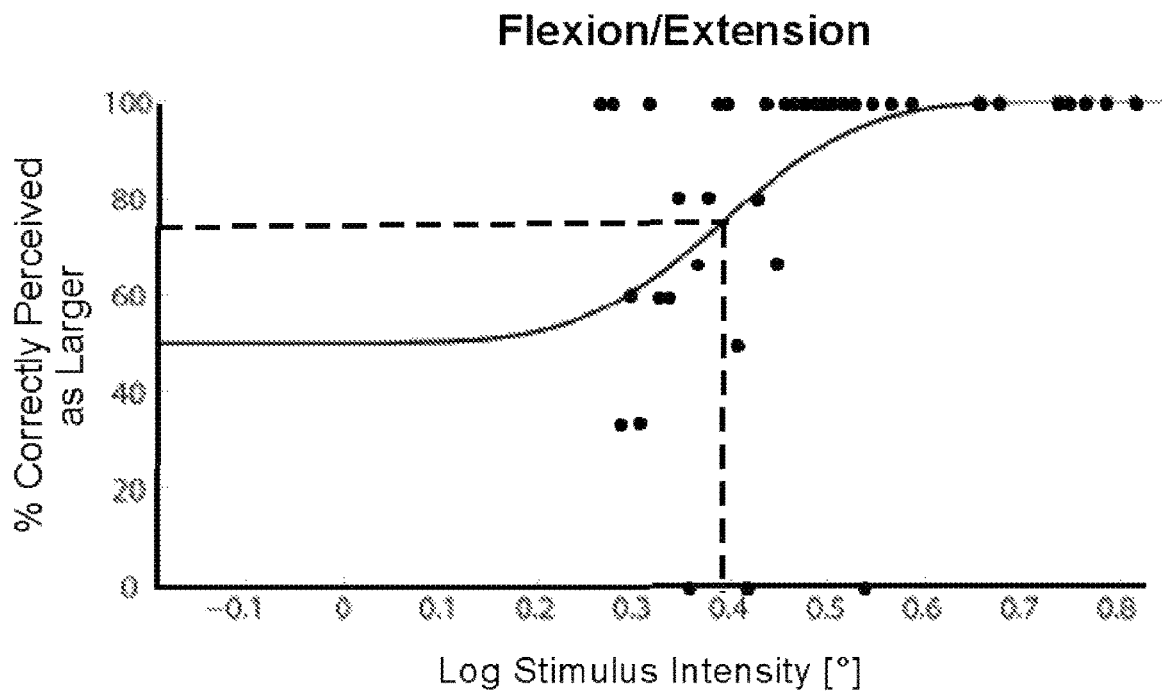
FIG. 14 is a plot of psychometric function for a subject of the testing described in the Examples section in the FE plane.
Figure 15:
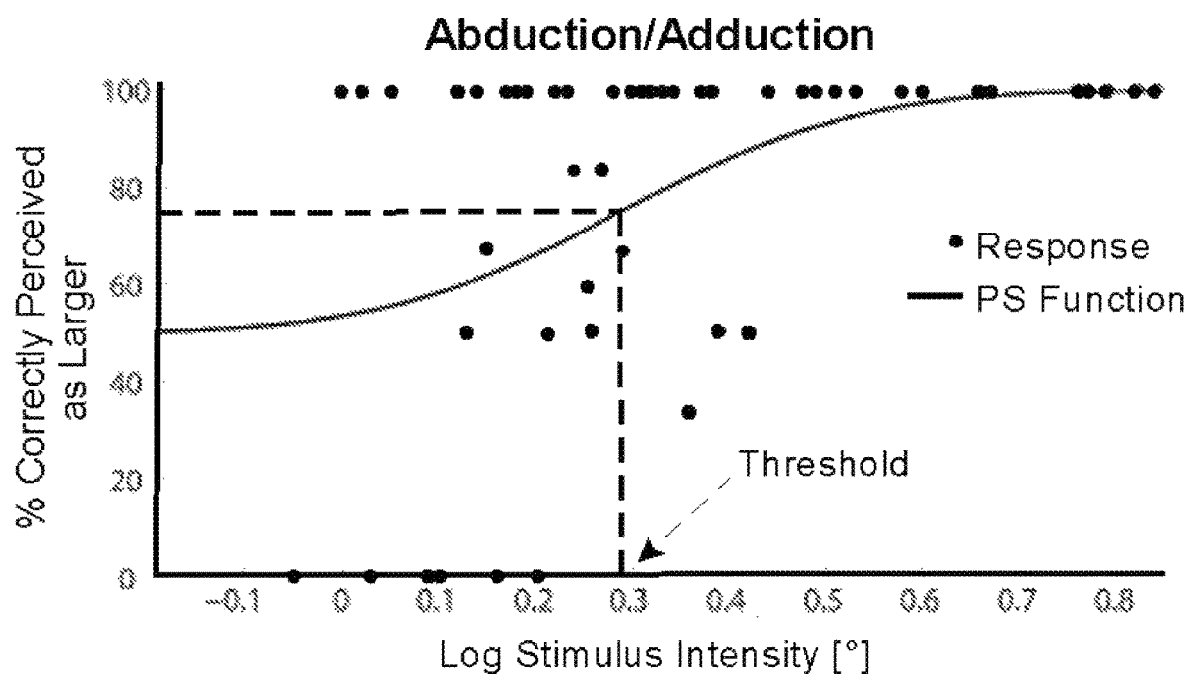
FIG. 15 is a plot of psychometric function in the AA plane for a subject of the testing described in the Examples section.

Exemplar response data of a single subject are shown in FIG. 13. During testing the differences between standard and comparison stimulus progressively converged towards a minimum, typically after approximately 40-70 trials. Data were visually inspected to verify the absence of lapsing errors in the upper asymptote, as these errors considerably affect the shape of the curve introducing bias in threshold estimates. FIGS. 14 and 15 show typical psychometric functions obtained for threshold detection in the two DOFs of the wrist joint.

Figure 16:
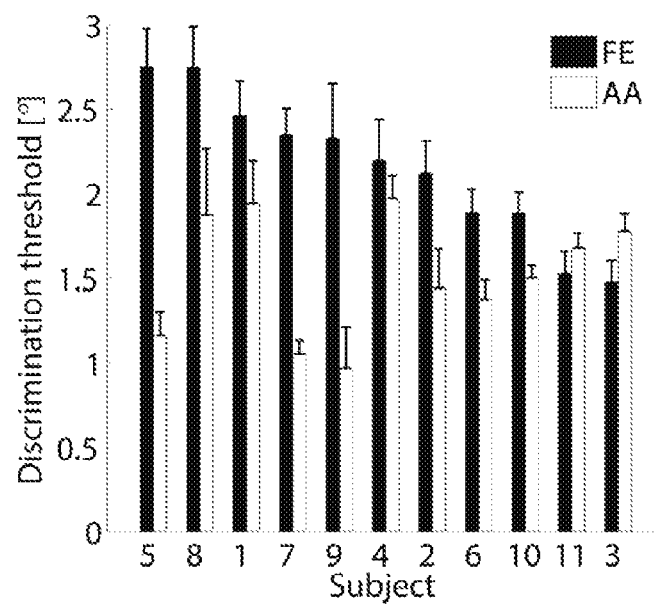
FIG. 16 is a graph of discrimination thresholds and standard deviations of the testing described in the Examples section.
Figure 17:
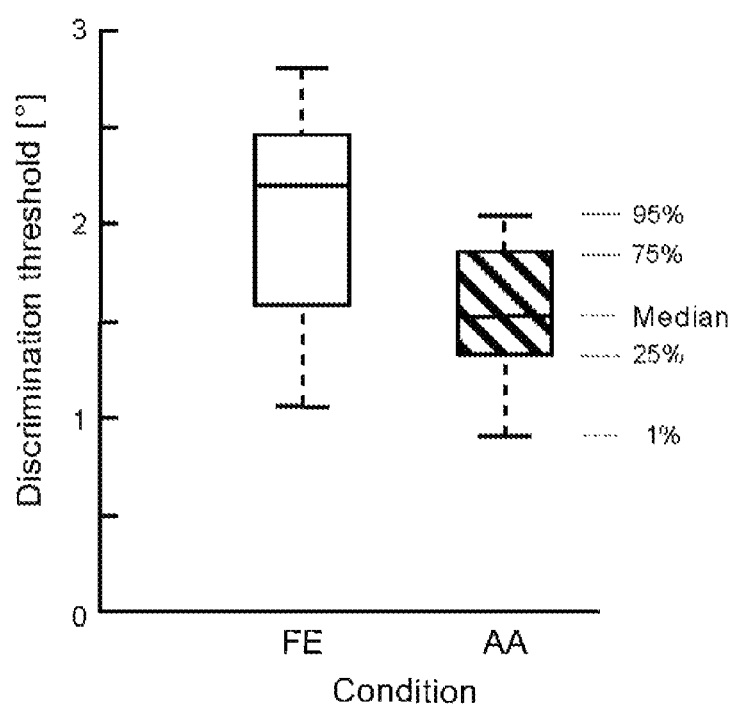
FIG. 17 is a box plot of thresholds in the FE and AA conditions for the testing described in the Examples section.
Figure 18:
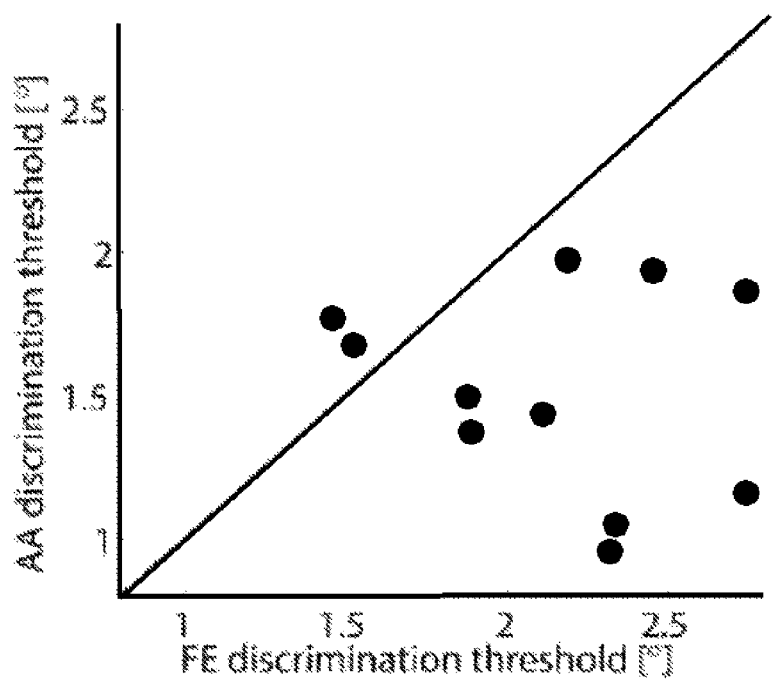
FIG. 18 is a graph of FE discrimination thresholds versus AA discrimination thresholds for the testing described in the Examples section.

The single subject data in FIGS. 14 and 15 reveal that this subject had a higher discrimination threshold for FE when compared to AA, yet was less certain about his judgments for AA (shallower slope of the function). With respect to the complete sample, nine of the 11 subjects exhibited FE thresholds that were higher than for AA indicating that both DOF have distinct acuities. Mean threshold for FE was 2.15°±0.43° and 1.52°±0.36° for AA. A subsequent one-way Analysis of Variance indicated that the mean thresholds for each DF were significantly different from each other (p=0.0013). FIGS. 16 and 17 summarize the thresholds for all the subjects, reporting the mean and the standard deviation. The two subjects with a lower proprioceptive acuity in FE compared to AA condition are the ones that performed best in the FE test: 1.47° and 1.52° for subjects 3 and 11 respectively as better noticeable in FIG. 18.

Figure 19:
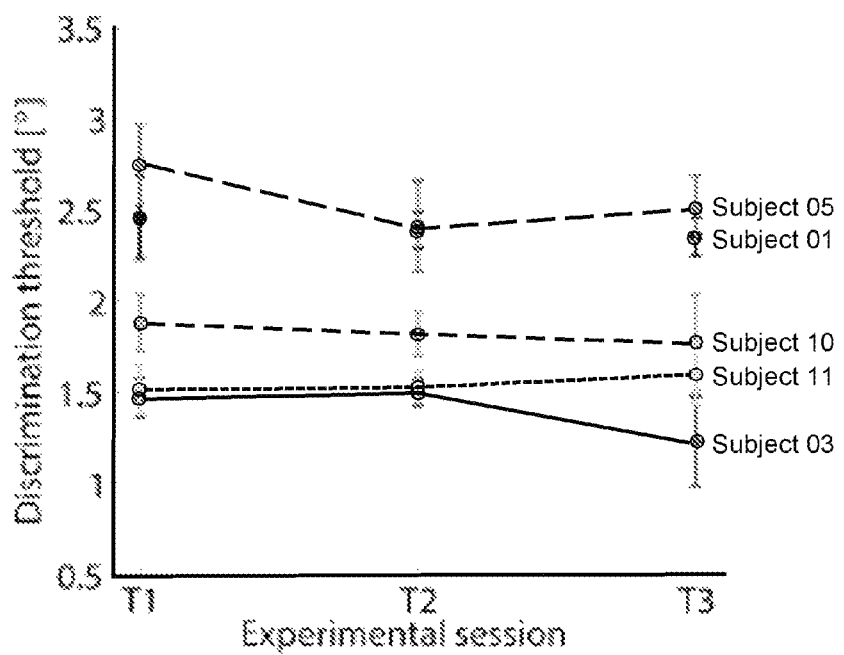
FIG. 19 is a plot of discrimination thresholds for FE conditions across three different experimental sessions of the testing described in the Examples section.

A subset of 5 subjects was retested under the identical experimental procedure for the FE condition resulting in a total of three different test sessions performed in three different days. Results are shown in FIG. 19, where negligible inter-test variability is observable ensuring that the method is time independent and test-retest reliable.

The feasibility of a three degrees-of-freedom wrist robot system was evaluated to determine proprioceptive discrimination thresholds for two different DOF of the wrist. Specifically, three goals were pursued. First, to establish data validity meaning that the system produces measures of proprioceptive acuity that are in accordance to previously published results on proprioceptive acuity of the human wrist. Second, to show that the system is sensitive to detect small differences in acuity. Third, to establish values for the test-retest reliability of the system indicating that the approach provides reliable estimates of proprioceptive acuity over repeated testing.

The above approach yielded proprioceptive thresholds for two DOF of the human wrist. Mean discrimination threshold for FE was 2.15° and 1.52° for AA. When expressing these thresholds with respect to the standard displacement of 15°, the threshold for FE is about 14.3% of the size of the standard and approximately 10.1% for the AA DOF.

Proprioceptive acuity of the upper limb joints have been measured and reported by previous studies. Unfortunately, no norm data on human wrist joint acuity are available and most previous studies used a joint position matching paradigms to assess proprioceptive function. Employing such a joint position matching paradigm, Lephart (1994) showed repositioning errors in the range of 12-31% of the target joint angle in normal shoulder joints. In a recent review, Goble (2010) reported absolute position matching errors in the magnitude of 2.5° for the elbow joint. Even though these studies are not directly comparable with the current results because they reflect proprioceptive acuity of the elbow and not the wrist and were measured by joint position matching paradigms, they nevertheless serve as an estimate of the expected proprioceptive acuity of upper limb joints. A recent study by Elangovan (2014) using the same psychophysical approach as the systems of the present disclosure reported a mean elbow joint discrimination threshold of 1.05°, which was approximately 10% of the standard of 10°. This finding coincides very closely with the results obtained by the systems of the present disclosure at the wrist joint. Moreover, because the above analyses use a psychophysical method, the results should provide a more precise acuity measure for the wrist joint. The same study by Elangovan (2014) also revealed that psychophysical thresholds were the most precise and least variable acuity measure.

The psychophysical estimate was significantly lower than mean position errors obtained by ipsi- or contralateral joint position matching tasks (ipsilateral: 1.51°; contralateral: 1.84°)—a 44% to 75% difference in measurement accuracy. These findings underline that measurements of wrist joint acuity with the systems of the present disclosure are within the previously reported physiological range of upper limb acuity, demonstrating that the systems of the present disclosure are capable of producing valid and accurate measures of wrist joint acuity.

Furthermore it was found that the acuity for AA is significantly higher than for FE. While this may be surprising on a first glance, it may be a very plausible finding if considering the neuroanatomy of the human wrist joint. It is known that the ligaments stabilizing the wrist contain mechanoreceptors, Ruffini and Pacini-like corpuscles, which contribute to wrist proprioception. Immunohistochemical studies of the wrist joint ligaments revealed a rich distribution of mechanoreceptors in the dorso-radial ligaments such as dorsal radiocarpal, dorsal intercarpal and scapholunate interosseous ligaments, a medium density in the volar and volar-triquetral ligaments, while others such as the long radiolunate ligament are nearly void of mechanoreceptors (Hagert, 2005; Hagert, 2007). The highly innervated dorso-radial ligaments are stressed during AA, while the lesser innervated ligaments such as the volar ligaments get primarily stressed during FE. These differences in mechanoreceptor density and innervation may ultimately lead to differences in acuity which is reflected in the differences in proprioceptive thresholds in the testing results. Furthermore the AA DOF has a lower range of motion than FE and forearm pronation/supination, and the presented stimuli (both standard and comparison) during the experiment scan a wide portion of the whole AA total range. The differences in the thresholds between the two DOFs highlighted the role of the structural differences in wrist joints and application of robotic technology can unveil the anisotropy of proprioceptive acuity among the different human joint, providing more insights also in motor learning and explaining why particular pattern of muscular activations are preferred for determined tasks.

Given that the thresholds are based on the verbal responses of a subject to a specific set of displacements, the sensitivity of the system is determined by the ability of the motors to create a precise displacement and by the sensitivity of the encoders recording the displacement. The resolution of the motors passively input the stimuli during the experiment is 0.2° for FE and 0.3° for AA, the resolution of the encoders is 0.0075° for FE and 0.0032° for AA. Motor and sensor resolution are well below the obtained proprioceptive thresholds, although it must be taken into account that quantization of motion and small joint misalignments of the wrist might introduce a certain level of inaccuracy even if negligible. Furthermore, the nature of the experimental paradigm (2-alternative-forced-choice discrimination paradigm) may also introduce a bias in subjects if they are not correctly trained before initiating the test. The experiments were designed in order to present the two stimuli (standard and comparison) pseudorandom either the first or the second stimulus throughout the whole task. To evaluate subjects' bias, the effect of stimulus order on the correct response was tested, and showed no differences. Therefore, it can be affirmed that the inherent limitations of both robotic technology and experimental paradigm do not jeopardize the application of robotic technology in the proprioceptive assessment.

To assess test-retest reliability of the threshold estimates, the above procedures were repeated for two additional times (T2 and T3) in five subjects only for the FE condition. The coefficients of test-retest reliability were r=0.986 for T2 with respect T1 and r=0.971 for T3 with respect to T2. The mean within-subject variability across all three tests was s=0.09. The results highlight excellent reliability. The proposed approach thus is repeatable, a key attribute of a quantitative measuring system. Given the precision of the motors and sensors, the most import source of variability of the threshold estimates across the sessions is likely the variability of a subject's verbal responses across different test dates to identical stimuli.

Although robotic technology has been widely promoted for use in rehabilitation (Dechaumont-Palacin, 2008; Prange, 2006), its application for diagnostics of proprioceptive function is still in its infancy. It is believed that no previous studies using haptic-capable robotic devices reported wrist proprioceptive discrimination thresholds for joint position sense. Based on established psychophysical assessment methods known to produce reliable and accurate results for quantification of proprioceptive discrimination thresholds (Elangovan, 2014), the present disclosure employs a robotic device to accurately deliver in a repetitive way position stimuli in two different anatomical planes of movement and consequently measured wrist proprioceptive acuity. The findings provide evidence for the feasibility of robotic-aided proprioceptive assessment. They further supported a standard paradigm for proprioceptive discrimination thresholds in human upper limb which should not be limited to the distal part of the arm but should be extended to different anatomical districts for multi joint investigation in future studies.

The data collected pursuant to the Examples of the present disclosure allowed the determination of the proprioceptive acuity thresholds of FE and AA DOFs of human wrist joint in healthy subjects. Beyond its neuroscientific relevance, this result introduces, for the first time, the use of a robotic interface to assess proprioceptive acuity of the wrist joint. It has been shown that the technology can generate robust, reliable and unbiased measures of proprioceptive function that allow for the efficient quantification of proprioceptive status and dysfunction. The use of a robotic system provides multiple advantages: it increases measurement resolution and precision, has good test-retest repeatability, avoids the problem of poor inter-rater reliability common in many clinical scales and reduces the variability of the reported outcome measures. Consequently, if properly employed, it can reduce costs by reducing the reliance of a clinician or therapist to obtain proprioceptive diagnostics.

The above findings support the use of an integrated robotic device to deliver rehabilitation in the form of sensory and motor intervention as well as to assess the progress in proprioception occurring as a result of the robotic intervention in an unbiased manner. Such a device apart from providing multimodal sensory feedback (visual, tactile and haptic) can also be used to deliver and modify treatment interventions based on the monitored progress in proprioceptive recovery. An integrated haptic robotic device that can assess proprioception, monitor subject progress in proprioception and deliver rehabilitation training may increase the efficiency of training and reduce the amount of individual attention needed from the clinician. This integration can be implemented with additional software and minimal hardware enhancements. Although this integrated device will automate the assessment and rehabilitative procedure, it may not entirely replace a clinician who can deliver sophisticated personal human interaction.

Although the present disclosure has been described with reference to preferred embodiments, workers skilled in the art will recognize that changes can be made in form and detail without departing from the spirit and scope of the present disclosure. For example, while the treatment systems of the present disclosure have been described with reference to assessment (and possible training) of proprioceptive function, other applications are envisioned. In other embodiments, the systems of the present disclosure can be useful to correlated wrist motion to brain activity, to study wrist movement control in impaired and unimpaired subject, as a high performance joystick as general interface for aerospace and aeronautical industry applications, etc.

What is claimed is:

1. A system for treating wrist joint proprioception, the system comprising:
a manipulandum unit including:
a base configured to support a subject's forearm,
a handle configured to be gripped by a subject's palm,
a linkage assembly connecting the handle to the base, the linkage assembly establishing three degrees of freedom of movement of the handle relative to the base,
a plurality of motors operatively connected to the linkage assembly, wherein each of the plurality of motors is provided with a sensor; and
a controller electronically connected to the manipulandum unit and programmed to:
actuate each of the plurality of motors,
receive feedback information from each sensor of the plurality of motors,
perform a proprioception assessment operation for objectively measuring proprioceptive function of a subject's wrist joint, including actuating at least one of the plurality of motors to effectuate movement of the handle relative to the base in a pre-determined manner, the assessment operation including a position sense routine in which the plurality of motors are actuated, based on the feedback information, by the controller to:
establish a reference position of the handle relative to the base,
move the handle about a first axis from the reference position to a standard position, and from the standard position to the reference position,
move the handle about the first axis from the reference position to a first comparison position, and from the first comparison position to the reference position,
wherein the controller is programmed to establish a pre-determined difference between the standard position and the first comparison position, and further wherein a subject's ability to perceive the difference is indicative of a subject's proprioceptive wrist position sense acuity as an objective measure of a subject's wrist joint proprioceptive function.

2. The system of claim 1, wherein the controller is programmed such that the position sense routine includes the controller actuating the plurality of motors to move the handle about the first axis from the reference position to a second comparison position, and from the second comparison position to the reference position, and further wherein a difference between the first and second comparison positions is pre-determined, and even further wherein a subject's ability to perceive the difference between the first and second comparison positions is indicative of a subject's proprioceptive wrist position sense acuity as an objective measure of a subject's wrist joint proprioceptive function.

3. The system of claim 1, wherein the controller is programmed such that the position sense routine further includes the controller actuating the plurality of motors to:
   move the handle about a second axis from the reference position to a second axis standard position, and from the second axis standard position to the reference position;
   move the handle about the second axis from the reference position to a second axis comparison position, and from the second axis comparison position to the reference position;
   wherein the second axis differs from the first axis;
      and further wherein the controller is programmed such that a difference between second axis standard position and the second axis comparison position is pre-determined, and even further wherein a subject's ability to perceive the difference between the second axis standard and comparison positions is indicative of proprioceptive wrist position sensor acuity as an objective measure of a subject's proprioceptive wrist position sense acuity.

4. The system of claim 3, wherein the controller is programmed such that the position sense routine further includes the controller actuating the plurality of motors to:
   move the handle about a third axis from the reference position to a third axis standard position, and from the third axis standard position to the reference position;
   move the handle about the third axis from the reference position to a third axis comparison position, and from the third axis comparison position to the reference position;
   wherein the third axis differs from the first and second axis;
   and further wherein the controller is programmed such that a difference between third axis standard position and the third axis comparison position is pre-determined, and even further wherein a subject's ability to perceive the difference between the third axis standard and reference positions is indicative of proprioceptive wrist position sense acuity as an objective measure of a subject's wrist joint proprioceptive function.

5. The system of claim 4, wherein in the system is configured such that the first axis corresponds with flexion-extension of a subject's wrist joint, the second axis corresponds with abduction-adduction of a subject's wrist joint, and the third axis corresponds with pronation-supination of a subject's hand.

6. The system of claim 1, wherein the proprioceptive function of the subject's wrist implicated by the position sense routine relates to detection of an absolute change in an articulated position of a subject's wrist joint.

7. The system of claim 1, wherein the proprioceptive function of the subject's wrist implicated by the position sense routine relates to discrimination between different articulated positions of a subject's wrist joint.

8. The system of claim 1, wherein the controller is further programmed to perform a motion sense routine in which the plurality of motors are actuated, based on the feedback information, by the controller to:
   move the handle about the first axis from the reference position at a first velocity;
   move the handle about the first axis from the reference position at a second velocity;
   wherein the controller is programmed to a establish a pre-determined difference between the first and second velocities, and further wherein a subject's ability to perceive the difference between the first and second velocities is indicative of proprioceptive wrist motion sense acuity as an objective measure of a subject's wrist joint proprioceptive function.

9. The system of claim 8, wherein the controller is programed such that the motion sense routine includes the controller actuating the plurality of motors to move the handle about the first axis from the reference position at a third velocity, and further wherein differences between the first, second and third velocities are pre-determined, and even further wherein a subject's ability to perceive the differences between the first, second, and third velocities is indicative of proprioceptive wrist motion sense acuity as an objective measure of a subject's wrist joint proprioceptive function.

10. The system of claim 8, wherein the controller is programmed such that the motion sense routine further includes the controller actuating the plurality of motors to:
   move the handle about a second axis from the reference position at a second axis first velocity;
   move the handle about the second axis from the reference position at a second axis second velocity;
   wherein the second axis differs from the first axis;
      and further wherein the controller is programmed such that a difference between second axis first velocity and the second axis second velocity is pre-determined,
      and even further wherein a subject's ability to perceive the difference between the second axis first and second velocities is indicative of proprioceptive wrist motion sense acuity as an objective measure of a subject's wrist joint proprioceptive function.

11. The system of claim 10, wherein the controller is programmed such that the motion sense routine further includes the controller actuating the plurality of motors to:
   move the handle about a third axis from the reference position at a third axis first velocity;
   move the handle about the third axis from the reference position at a third axis second velocity;
   wherein the third axis differs from the first and second axis;
      and further wherein the controller is programmed such that a difference between third axis first velocity and the third axis second velocity is pre-determined, and even further wherein a subject's ability to perceive the difference between the third axis first and second velocities is indicative of proprioceptive wrist motion sense acuity as an objective measure of a subject's wrist joint proprioceptive function.

12. The system of claim 8, wherein the proprioceptive function of the subject's wrist implicated by the motion sense routine implicates detection of movement of a subject's wrist joint.

13. The system of claim 8, wherein the proprioceptive function of the subject's wrist implicated by the motion sense routine implicates discrimination between different velocities of movement of a subject's wrist joint.

14. The system of claim 1, wherein the base establishes a reference axis for the manipulandum unit, and further wherein the linkage assembly is configured to establish the three degrees of freedom of movement at the manipulandum unit as:
   a first, flexion-extension (FE) movement in which the handle pivots relative to the base about the first or FE axis of the unit, the FE axis being perpendicular to the reference axis;
   a second, abduction-adduction (AA) movement in which the handle pivots relative to the base about an AA axis of the unit, the AA axis being perpendicular to the FE axis and to the reference axis; and a third, pronation-supination (PS) movement in which the handle pivots relative to the base about a PS axis of the unit, the PS axis being parallel with the reference axis.

15. The system of claim 14, wherein the plurality of motors includes a first motor connected to the linkage assembly so as to control articulation of the handle about the FE axis, second and third motors connected to the linkage assembly so as to control articulation of the handle about the AA axis, and a fourth motor connected to the linkage assembly so as to control articulation of the handle about the PS axis.

16. The system of claim 14, wherein the plurality of motors is configured to provide a range of motion of the handle relative to the base from the reference position of:
at least +−70 degrees about the FE axis;
at least +45 degrees/−27 degrees about the AA axis; and
at least +−75 degrees about the PS axis.

* * * * *